(12) United States Patent
Singh et al.

(10) Patent No.: US 8,741,331 B2
(45) Date of Patent: *Jun. 3, 2014

(54) HYDROGEL COMPOSITIONS WITH AN ERODIBLE BACKING MEMBER

(71) Applicant: Corium International, Inc., Menlo Park, CA (US)

(72) Inventors: Parminder Singh, Union City, CA (US); Adrian Faasse, Carmel Valley, CA (US); Gary W. Cleary, Los Altos Hills, CA (US); Sri Mudumba, Union City, CA (US); Mikhail M. Feldstein, Moscow (RU); Danir F. Bairamov, Irvine, CA (US)

(73) Assignees: A. V. Topchiev Institute of Petrochemicals Synthesis, Russian Academy of Sciences, Moscow (RU); Corium International, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/916,526

(22) Filed: Jun. 12, 2013

(65) Prior Publication Data

US 2013/0273127 A1  Oct. 17, 2013

Related U.S. Application Data

(63) Continuation of application No. 13/482,965, filed on May 29, 2012, now Pat. No. 8,481,071, which is a continuation of application No. 10/661,103, filed on Sep. 12, 2003, now Pat. No. 8,206,738, which is a continuation-in-part of application No. 10/359,548, filed on Feb. 5, 2003, which is a continuation-in-part of application No. 10/137,664, filed on May 1, 2002.

(60) Provisional application No. 60/288,008, filed on May 1, 2001.

(51) Int. Cl.
*A61F 6/14* (2006.01)
*A61F 13/00* (2006.01)
*A61F 13/02* (2006.01)
*A61L 15/16* (2006.01)
*A61K 9/70* (2006.01)
*A61K 9/14* (2006.01)

(52) U.S. Cl.
USPC ........... 424/434; 424/435; 424/443; 424/448; 424/449; 424/488; 424/487; 424/484

(58) Field of Classification Search
None
See application file for complete search history.

(56) References Cited

U.S. PATENT DOCUMENTS

| | | |
|---|---|---|
| 2,561,071 A | 7/1951 | Prisk |
| 2,579,403 A | 12/1951 | Slomowitz et al. |
| 3,150,977 A | 9/1964 | Hart et al. |
| 3,689,439 A | 9/1972 | Field et al. |
| 3,721,657 A | 3/1973 | Seiderman |
| 3,749,755 A | 7/1973 | Bronstart et al. |
| 3,852,228 A | 12/1974 | Brothers |
| 3,957,605 A | 5/1976 | Assarsson et al. |
| 3,993,551 A | 11/1976 | Assarsson et al. |
| 3,996,934 A | 12/1976 | Zaffaroni |
| 4,091,090 A | 5/1978 | Sipos |
| 4,093,673 A | 6/1978 | Chang et al. |
| 4,160,020 A | 7/1979 | Ayer et al. |
| 4,231,369 A | 11/1980 | Sorensen et al. |
| 4,277,580 A | 7/1981 | Allen et al. |
| 4,325,851 A | 4/1982 | Colon et al. |
| 4,346,709 A | 8/1982 | Schmitt et al. |
| 4,367,732 A | 1/1983 | Poulsen et al. |
| 4,492,685 A | 1/1985 | Keith et al. |
| 4,529,601 A | 7/1985 | Broberg et al. |
| 4,552,751 A | 11/1985 | Inaba et al. |
| 4,557,934 A | 12/1985 | Cooper |
| 4,562,060 A | 12/1985 | Broberg et al. |
| 4,568,343 A | 2/1986 | Leeper et al. |
| 4,587,289 A | 5/1986 | Comert et al. |
| 4,593,053 A | 6/1986 | Jevne et al. |
| 4,624,665 A | 11/1986 | Nuwayser |
| 4,699,146 A | 10/1987 | Sieverding |
| 4,713,243 A | 12/1987 | Schiraldi et al. |
| 4,743,249 A | 5/1988 | Loveland |
| 4,750,482 A | 6/1988 | Sieverding |

(Continued)

FOREIGN PATENT DOCUMENTS

| | | |
|---|---|---|
| CA | 2402021 | 9/2001 |
| CA | 2451431 | 1/2003 |

(Continued)

OTHER PUBLICATIONS

U.S. Appl. No. 11/150,811, filed Jun. 10, 2005, Feldstein et al.
U.S. Appl. No. 12/687,586, filed Jan. 11, 2009, Singh et al.

(Continued)

*Primary Examiner* — Isis Ghali
(74) *Attorney, Agent, or Firm* — Judy M. Mohr; McDermott Will & Emery LLP

(57) ABSTRACT

A composition is provided, wherein the composition comprises a water-swellable, water-insoluble polymer, a blend of a hydrophilic polymer with a complementary oligomer capable of hydrogen or electrostatic bonding to the hydrophilic polymer. The composition also includes a backing member. Active ingredients, such as a whitening agent, may be included. The composition finds utility as an oral dressing, for example, a tooth whitening composition that is applied to the teeth in need of whitening. The composition can be designed to be removed when the degree of whitening has been achieved or left in place and allowed to erode entirely. In certain embodiments, the composition is translucent. Methods for preparing and using the compositions are also disclosed.

6 Claims, No Drawings

(56) References Cited

U.S. PATENT DOCUMENTS

| | | |
|---|---|---|
| 4,771,105 A | 9/1988 | Shirai et al. |
| 4,849,224 A | 7/1989 | Chang et al. |
| 4,863,738 A | 9/1989 | Taskovich |
| 4,863,970 A | 9/1989 | Patel et al. |
| 4,867,748 A | 9/1989 | Samuelsen |
| 4,871,536 A | 10/1989 | Arraudeau et al. |
| 4,873,299 A | 10/1989 | Nawoakosky et al. |
| 4,877,628 A | 10/1989 | Stypula |
| 4,904,247 A | 2/1990 | Therriault et al. |
| 4,906,169 A | 3/1990 | Chien et al. |
| 4,927,408 A | 5/1990 | Haak et al. |
| 4,945,084 A | 7/1990 | Packman |
| 4,953,053 A | 8/1990 | Pratt |
| 4,973,468 A | 11/1990 | Chiang et al. |
| 4,983,395 A | 1/1991 | Chang et al. |
| 5,023,084 A | 6/1991 | Chien et al. |
| 5,053,227 A | 10/1991 | Chiang et al. |
| 5,057,500 A | 10/1991 | Thornfelt |
| 5,073,381 A | 12/1991 | Ivan et al. |
| 5,102,662 A | 4/1992 | Gallagher |
| 5,125,894 A | 6/1992 | Phipps et al. |
| 5,133,970 A | 7/1992 | Petereit et al. |
| 5,141,750 A | 8/1992 | Lee et al. |
| 5,173,302 A | 12/1992 | Holmblad et al. |
| 5,183,901 A | 2/1993 | Login et al. |
| 5,196,405 A | 3/1993 | Packman |
| 5,200,190 A | 4/1993 | Azuma et al. |
| 5,206,385 A | 4/1993 | Login et al. |
| 5,224,928 A | 7/1993 | Sibalis et al. |
| 5,232,702 A | 8/1993 | Pfister et al. |
| 5,234,690 A | 8/1993 | Chiang et al. |
| 5,234,957 A | 8/1993 | Mantelle |
| 5,240,995 A | 8/1993 | Gyory et al. |
| 5,254,346 A | 10/1993 | Tucker et al. |
| 5,270,358 A | 12/1993 | Asmus |
| 5,276,079 A | 1/1994 | Duan et al. |
| 5,296,512 A | 3/1994 | Beier et al. |
| 5,300,291 A | 4/1994 | Sablotsky et al. |
| 5,310,563 A | 5/1994 | Curtis et al. |
| 5,322,689 A | 6/1994 | Hughes et al. |
| 5,326,685 A | 7/1994 | Gaglio et al. |
| 5,332,576 A | 7/1994 | Mantelle |
| 5,338,490 A | 8/1994 | Dietz et al. |
| 5,342,623 A | 8/1994 | Enscore et al. |
| 5,344,394 A | 9/1994 | Gyory et al. |
| 5,354,823 A | 10/1994 | Tseng et al. |
| 5,362,420 A | 11/1994 | Itoh et al. |
| 5,376,377 A | 12/1994 | Gale et al. |
| 5,422,119 A | 6/1995 | Casper |
| 5,438,076 A | 8/1995 | Friedman et al. |
| 5,446,070 A | 8/1995 | Mantelle |
| 5,456,745 A | 10/1995 | Roreger et al. |
| 5,462,743 A | 10/1995 | Turner et al. |
| 5,462,745 A | 10/1995 | Enscore et al. |
| 5,492,943 A | 2/1996 | Stempel |
| 5,508,024 A | 4/1996 | Tranner |
| 5,508,367 A | 4/1996 | Zajaczkowski |
| 5,527,271 A | 6/1996 | Shah et al. |
| 5,543,148 A | 8/1996 | Lapidus |
| 5,563,153 A | 10/1996 | Mueller et al. |
| 5,575,654 A | 11/1996 | Fontenot |
| 5,593,686 A | 1/1997 | Kissel et al. |
| 5,594,068 A | 1/1997 | Buchanan et al. |
| 5,599,373 A | 2/1997 | Zanuccoli |
| 5,614,178 A | 3/1997 | Bloon et al. |
| 5,631,267 A | 5/1997 | Gleich et al. |
| 5,633,010 A | 5/1997 | Chen |
| 5,641,504 A | 6/1997 | Lee et al. |
| 5,641,507 A | 6/1997 | DeVillez |
| 5,643,187 A | 7/1997 | Naestoft et al. |
| 5,645,062 A | 7/1997 | Anderson et al. |
| 5,645,855 A | 7/1997 | Lorenz |
| 5,656,286 A | 8/1997 | Miranda et al. |
| 5,660,178 A | 8/1997 | Kantner et al. |
| 5,662,925 A | 9/1997 | Ebert et al. |
| 5,663,010 A | 9/1997 | Stocchiero |
| 5,674,561 A | 10/1997 | Dietz et al. |
| 5,700,478 A | 12/1997 | Biegajski et al. |
| 5,702,721 A | 12/1997 | Horstmann et al. |
| 5,718,187 A | 2/1998 | Pollock et al. |
| 5,718,886 A | 2/1998 | Pellico |
| 5,719,197 A | 2/1998 | Kanios et al. |
| 5,723,145 A | 3/1998 | Shikinami et al. |
| 5,725,876 A | 3/1998 | Mantelle et al. |
| 5,726,250 A | 3/1998 | Zajaczkowski |
| 5,730,999 A | 3/1998 | Lehmann et al. |
| 5,744,155 A | 4/1998 | Freidman et al. |
| 5,762,956 A | 6/1998 | Chien et al. |
| 5,770,220 A | 6/1998 | Meconi et al. |
| 5,773,490 A | 6/1998 | Shikinami et al. |
| 5,780,050 A | 7/1998 | Jain et al. |
| 5,785,527 A | 7/1998 | Jensen et al. |
| 5,785,976 A | 7/1998 | Westesen et al. |
| 5,788,983 A | 8/1998 | Chien et al. |
| 5,800,832 A | 9/1998 | Tapolsky et al. |
| 5,804,611 A | 9/1998 | Takoh et al. |
| 5,827,213 A | 10/1998 | Jensen |
| 5,827,525 A | 10/1998 | Liao et al. |
| 5,830,932 A | 11/1998 | Kay |
| 5,837,713 A | 11/1998 | Gleich et al. |
| 5,843,472 A | 12/1998 | Ma et al. |
| 5,846,558 A | 12/1998 | Nielsen et al. |
| 5,851,549 A | 12/1998 | Svec |
| 5,853,755 A | 12/1998 | Foldvari |
| 5,858,332 A | 1/1999 | Jensen et al. |
| 5,858,410 A | 1/1999 | Muller et al. |
| 5,863,662 A | 1/1999 | Hornby et al. |
| 5,876,746 A | 3/1999 | Jona et al. |
| 5,879,691 A | 3/1999 | Sagel et al. |
| 5,879,701 A | 3/1999 | Audett et al. |
| 5,891,453 A | 4/1999 | Sagel et al. |
| 5,894,017 A | 4/1999 | Sagel et al. |
| 5,900,249 A | 5/1999 | Smith |
| 5,902,598 A | 5/1999 | Chen et al. |
| 5,911,980 A | 6/1999 | Samour et al. |
| 5,912,271 A | 6/1999 | Brodine et al. |
| 5,916,587 A | 6/1999 | Min et al. |
| 5,942,543 A | 8/1999 | Ernst |
| 5,945,032 A | 8/1999 | Breitenbach et al. |
| 5,945,457 A | 8/1999 | Plate et al. |
| 5,948,416 A | 9/1999 | Wagner et al. |
| 5,948,430 A | 9/1999 | Zerbe et al. |
| 5,948,433 A | 9/1999 | Burton et al. |
| 5,958,379 A | 9/1999 | Regenold et al. |
| 5,958,446 A | 9/1999 | Miranda et al. |
| 5,958,984 A | 9/1999 | Devillez |
| 5,962,011 A | 10/1999 | DeVillez |
| 5,972,377 A | 10/1999 | Jona et al. |
| 5,976,565 A | 11/1999 | Fotinos |
| 5,985,311 A | 11/1999 | Cordes et al. |
| 5,985,860 A | 11/1999 | Toppo |
| 5,985,990 A | 11/1999 | Kantner et al. |
| 5,989,569 A | 11/1999 | Dirksing et al. |
| 5,990,179 A | 11/1999 | Gyori et al. |
| 5,993,836 A | 11/1999 | Castillo |
| 5,993,849 A | 11/1999 | Assmus et al. |
| 5,997,886 A | 12/1999 | Peffly et al. |
| 6,004,566 A | 12/1999 | Freidman et al. |
| 6,004,578 A | 12/1999 | Lee et al. |
| 6,007,837 A | 12/1999 | Enscore et al. |
| 6,024,976 A | 2/2000 | Miranda et al. |
| 6,045,811 A | 4/2000 | Dirksing et al. |
| 6,051,609 A | 4/2000 | Yu et al. |
| 6,063,399 A | 5/2000 | Assmus et al. |
| 6,068,650 A | 5/2000 | Hofmann et al. |
| 6,072,100 A | 6/2000 | Mooney et al. |
| 6,075,626 A | 6/2000 | Mizutani et al. |
| 6,083,421 A | 7/2000 | Huang et al. |
| 6,093,328 A | 7/2000 | Santina |
| 6,096,328 A | 8/2000 | Sagel et al. |
| 6,135,126 A | 10/2000 | Joshi |
| 6,142,939 A | 11/2000 | Eppstein et al. |
| 6,146,654 A | 11/2000 | Kubo |
| 6,153,215 A | 11/2000 | Samuelsen et al. |

(56) References Cited

U.S. PATENT DOCUMENTS

| | | | |
|---|---|---|---|
| 6,162,456 A | 12/2000 | Dunbar et al. |
| 6,165,499 A | 12/2000 | Kleinsorgen et al. |
| 6,177,096 B1 | 1/2001 | Zerbe et al. |
| 6,193,993 B1 | 2/2001 | Murahashi et al. |
| 6,197,331 B1 | 3/2001 | Lerner et al. |
| 6,201,164 B1 | 3/2001 | Wulff et al. |
| 6,212,671 B1 | 4/2001 | Kanehira et al. |
| 6,221,341 B1 | 4/2001 | Montgomery |
| 6,221,383 B1 | 4/2001 | Miranda et al. |
| 6,231,885 B1 | 5/2001 | Carrarra |
| 6,248,363 B1 | 6/2001 | Patel et al. |
| 6,264,981 B1 | 7/2001 | Zhang et al. |
| 6,270,792 B1 | 8/2001 | Guillemet et al. |
| 6,275,728 B1 | 8/2001 | Venkatraman et al. |
| 6,306,370 B1 | 10/2001 | Jensen et al. |
| 6,312,666 B1 | 11/2001 | Oxman et al. |
| 6,312,670 B1 | 11/2001 | Montgomery |
| 6,316,022 B1 | 11/2001 | Mantelle et al. |
| 6,322,774 B1 | 11/2001 | Jensen et al. |
| 6,329,472 B1 | 12/2001 | Kim et al. |
| 6,368,576 B1 | 4/2002 | Jensen et al. |
| 6,419,905 B1 | 7/2002 | Alvarez Hernandez |
| 6,419,906 B1 | 7/2002 | Xu et al. |
| 6,451,240 B1 | 9/2002 | Sherman et al. |
| 6,451,777 B1 | 9/2002 | Bradbury et al. |
| 6,461,636 B1 | 10/2002 | Arth et al. |
| 6,488,913 B2 | 12/2002 | Orlowski et al. |
| 6,517,350 B2 | 2/2003 | Diasti et al. |
| 6,552,147 B2 | 4/2003 | Parker et al. |
| 6,558,654 B2 | 5/2003 | McLaughlin |
| 6,562,363 B1 | 5/2003 | Mantelle et al. |
| 6,576,712 B2 | 6/2003 | Feldstein et al. |
| 6,585,997 B2 | 7/2003 | Moro et al. |
| 6,591,124 B2 | 7/2003 | Sherman et al. |
| 6,596,298 B2 | 7/2003 | Leung et al. |
| 6,602,912 B2 | 8/2003 | Hsu et al. |
| 6,611,706 B2 | 8/2003 | Avrahami et al. |
| 6,638,528 B1 | 10/2003 | Kanios |
| 6,656,493 B2 | 12/2003 | Dzija |
| 6,667,410 B2 | 12/2003 | Magnus et al. |
| 6,673,363 B2 | 1/2004 | Luo et al. |
| 6,682,721 B2 | 1/2004 | Kim et al. |
| 6,689,344 B2 | 2/2004 | Chang et al. |
| 6,696,459 B1 | 2/2004 | Jones et al. |
| 6,708,060 B1 | 3/2004 | Avrahami et al. |
| 6,709,671 B2 | 3/2004 | Zerbe et al. |
| 6,711,435 B2 | 3/2004 | Avrahami |
| 6,714,497 B2 | 3/2004 | Yeo et al. |
| 6,750,291 B2 | 6/2004 | Kim et al. |
| 6,759,030 B2 | 7/2004 | Kosti |
| 6,762,202 B2 | 7/2004 | Marek et al. |
| 6,780,401 B2 | 8/2004 | Kim et al. |
| 6,783,769 B1 | 8/2004 | Arth et al. |
| 6,803,420 B2 | 10/2004 | Cleary et al. |
| 6,805,874 B1 | 10/2004 | Lutz et al. |
| 6,806,308 B2 | 10/2004 | Zajac |
| 6,884,833 B2 | 4/2005 | Cheang et al. |
| 6,946,142 B2 | 9/2005 | Chang et al. |
| 6,962,691 B1 | 11/2005 | Lulla et al. |
| 7,078,359 B2 | 7/2006 | Stepanian et al. |
| 7,112,713 B2 | 9/2006 | Sceusa |
| 7,122,199 B2 | 10/2006 | Sagel et al. |
| 7,138,458 B2 | 11/2006 | Cleary et al. |
| 7,217,853 B2 | 5/2007 | Kulichikhin et al. |
| 7,323,161 B2 | 1/2008 | Choi et al. |
| 7,384,650 B2 | 6/2008 | Chien |
| 7,456,331 B2 | 11/2008 | Kulichikhin et al. |
| 7,744,918 B2 | 6/2010 | Yamaguchi et al. |
| 8,206,738 B2 | 6/2012 | Singh et al. |
| 8,273,405 B2 | 9/2012 | Feldstein et al. |
| 8,481,059 B2 | 7/2013 | Cleary et al. |
| 8,481,071 B2 | 7/2013 | Singh et al. |
| 2001/0006677 A1 | 7/2001 | Mcginty et al. |
| 2001/0021374 A1 | 9/2001 | Montgomery |
| 2001/0046471 A1 | 11/2001 | Marek et al. |
| 2002/0004190 A1 | 1/2002 | Diasti et al. |
| 2002/0009420 A1 | 1/2002 | McLaughlin |
| 2002/0048602 A1 | 4/2002 | Flore et al. |
| 2002/0076487 A1 | 6/2002 | Zajac |
| 2002/0106335 A1 | 8/2002 | Orlowski et al. |
| 2002/0131990 A1 | 9/2002 | Barkalow et al. |
| 2002/0197284 A1 | 12/2002 | Luo et al. |
| 2003/0035841 A1 | 2/2003 | Dzija |
| 2003/0055190 A1 | 3/2003 | Parker et al. |
| 2003/0068376 A1 | 4/2003 | Chen et al. |
| 2003/0100654 A1 | 5/2003 | Cheang et al. |
| 2003/0101507 A1 | 6/2003 | Cleary et al. |
| 2003/0103427 A1 | 6/2003 | Yeo et al. |
| 2003/0104041 A1 | 6/2003 | Hsu et al. |
| 2003/0152528 A1 | 8/2003 | Singh et al. |
| 2003/0152615 A1 | 8/2003 | Houze et al. |
| 2003/0170308 A1 | 9/2003 | Cleary et al. |
| 2003/0180229 A1 | 9/2003 | Kosti |
| 2003/0225356 A1 | 12/2003 | Kulichikhin et al. |
| 2003/0235549 A1 | 12/2003 | Singh et al. |
| 2004/0005277 A1 | 1/2004 | Willison et al. |
| 2004/0053901 A1 | 3/2004 | Chien |
| 2004/0105834 A1 | 6/2004 | Singh et al. |
| 2004/0136927 A1 | 7/2004 | Kim et al. |
| 2004/0166147 A1 | 8/2004 | Lundy et al. |
| 2004/0219111 A1 | 11/2004 | Kim et al. |
| 2004/0258723 A1 | 12/2004 | Singh et al. |
| 2005/0031554 A1 | 2/2005 | Kim et al. |
| 2005/0113510 A1 | 5/2005 | Feldstein et al. |
| 2005/0208110 A1 | 9/2005 | Singh et al. |
| 2005/0215727 A1 | 9/2005 | Feldstein et al. |
| 2005/0228113 A1 | 10/2005 | Baumer et al. |
| 2005/0256223 A1 | 11/2005 | Kolb et al. |
| 2006/0034905 A1 | 2/2006 | Singh et al. |
| 2006/0110434 A1 | 5/2006 | Yamaguchi et al. |
| 2006/0168905 A1 | 8/2006 | Blanc et al. |
| 2006/0171906 A1 | 8/2006 | Singh et al. |
| 2006/0182788 A1 | 8/2006 | Singh et al. |
| 2006/0193793 A1 | 8/2006 | Kim et al. |
| 2006/0193794 A1 | 8/2006 | Kim et al. |
| 2008/0161492 A1 | 7/2008 | Cleary et al. |
| 2009/0155343 A1 | 6/2009 | Kawahara et al. |
| 2009/0258060 A1 | 10/2009 | Cleary et al. |
| 2012/0027695 A1 | 2/2012 | Feldstein et al. |
| 2012/0237579 A1 | 9/2012 | Singh et al. |
| 2012/0321569 A1 | 12/2012 | Feldstein et al. |

FOREIGN PATENT DOCUMENTS

| | | |
|---|---|---|
| CA | 2506073 | 6/2004 |
| CA | 2515128 A1 | 8/2004 |
| CA | 2579492 | 3/2006 |
| CA | 2520986 | 4/2006 |
| DE | 8509793 | 5/1985 |
| DE | 4219368 | 6/1992 |
| EP | 0184470 | 6/1986 |
| EP | 0303445 | 2/1989 |
| EP | 0364211 | 4/1990 |
| EP | 0371421 | 6/1990 |
| EP | 0511782 | 11/1992 |
| EP | 0516026 | 12/1992 |
| EP | 0545594 | 6/1993 |
| EP | 0581581 | 2/1994 |
| EP | 0672094 | 9/1995 |
| EP | 0737477 | 10/1996 |
| EP | 0838225 | 4/1998 |
| EP | 0848960 | 6/1998 |
| EP | 1066823 | 1/2001 |
| EP | 2005952 A1 | 12/2008 |
| GB | 1108837 | 4/1968 |
| JP | 58-162681 | 9/1983 |
| JP | 59-196817 | 11/1984 |
| JP | 01-151524 A | 6/1989 |
| JP | 03-066612 | 3/1991 |
| JP | 03-247334 | 5/1991 |
| JP | 03-275619 | 6/1991 |
| JP | 04-266818 | 2/1992 |
| JP | 06-100467 | 4/1994 |
| JP | 10-017448 | 1/1998 |

(56) References Cited

FOREIGN PATENT DOCUMENTS

| | | |
|---|---|---|
| JP | 2001-213768 A | 7/2001 |
| JP | 2002-029949 | 1/2002 |
| JP | 2002-145746 A | 5/2002 |
| KR | 20020045224 | 6/2002 |
| KR | 20030000299 | 1/2003 |
| KR | 20030000528 | 1/2003 |
| KR | 20030003969 | 1/2003 |
| KR | 20030003973 | 1/2003 |
| SU | 1459215 | 11/1995 |
| WO | WO 89/03859 | 5/1989 |
| WO | WO 90/07940 A1 | 7/1990 |
| WO | WO 93/02717 | 2/1993 |
| WO | WO 94/05340 | 3/1994 |
| WO | WO 96/19205 | 6/1996 |
| WO | WO 97/11676 | 4/1997 |
| WO | WO 98/20862 A1 | 5/1998 |
| WO | WO 98/26763 A1 | 6/1998 |
| WO | WO 98/37870 | 9/1998 |
| WO | WO 98/55044 | 12/1998 |
| WO | WO 99/11728 A1 | 3/1999 |
| WO | WO 99/17738 | 4/1999 |
| WO | WO 99/44678 | 9/1999 |
| WO | WO 99/47128 | 9/1999 |
| WO | WO 99/54422 | 10/1999 |
| WO | WO 99/55312 A2 | 11/1999 |
| WO | WO 00/16725 | 3/2000 |
| WO | WO 00/18365 A2 | 4/2000 |
| WO | WO 00/61120 A1 | 10/2000 |
| WO | WO 00/69421 | 11/2000 |
| WO | WO 01/01958 A1 | 1/2001 |
| WO | WO 01/07018 A1 | 2/2001 |
| WO | WO 01/26637 | 4/2001 |
| WO | WO 01/68045 | 9/2001 |
| WO | WO 01/87276 | 11/2001 |
| WO | WO 02/00182 A3 | 1/2002 |
| WO | WO 02/04570 | 1/2002 |
| WO | WO 03/000216 | 1/2002 |
| WO | WO 02/43657 | 6/2002 |
| WO | WO 02/067645 | 11/2002 |
| WO | WO 02/087642 | 11/2002 |
| WO | WO 02/089849 | 11/2002 |
| WO | WO 03/011259 A1 | 2/2003 |
| WO | WO 03/099344 | 12/2003 |
| WO | WO 03/101357 A1 | 12/2003 |
| WO | WO 2004/045569 | 6/2004 |
| WO | WO 2004/054638 | 7/2004 |
| WO | WO 2004/071323 | 8/2004 |
| WO | WO 03/089046 | 10/2004 |
| WO | WO 2004/093786 | 11/2004 |
| WO | WO 2004/103201 | 12/2004 |
| WO | WO 2005/027768 | 3/2005 |
| WO | WO 2005/074894 A1 | 8/2005 |
| WO | WO 2006/017807 | 2/2006 |
| WO | WO 2006/029407 | 3/2006 |
| WO | WO 2006/069236 | 6/2006 |
| WO | WO 2006/074173 | 7/2006 |
| WO | WO 2006/081497 | 8/2006 |
| WO | WO 2006/124639 | 11/2006 |
| WO | WO 2007/119656 | 10/2007 |
| WO | WO 2010/083035 | 7/2010 |

OTHER PUBLICATIONS

"Aquasorb® A-500 Cellulose Gum (CMC)", Hercules Incorporated, Aqualon Division, Product Data No. 4234, 2 pgs, (2005).
International Search Report for PCT/US2010/000081 Mailed Sep. 7, 2010.
Aubin et al., "Analysis of the glass transition temperature of miscible polymer blends", Macromolecules, vol. 21, pp. 2945-2949, (1988).
Bairamov et al., "Kinetic parameters of poly(N-vinyl pyrrolidone) spontaneous mixing with short-chain poly(ethylene glycol)", Polym. Mater. Sci. Eng., vol. 82, pp. 7-8, (2000).
Barbucci et al., "Swelling behavior of carboxymethylcellulose hydrogels in relation to cross-linking, pH, and charge density", Macromolecules, vol. 33, No. 20, pp. 7475-7478 (2000).
Borodulina et al., "Viscoelasticity of Pressure-sensitive adhesive and bioadhesive Hydrogels under compressive load", Proceed. 24th Annual Meeting Adhesion Soc., pp. 147-149, (2001).
Chalykh et al., "Effects of composition and hydration on adhesive properties of poly(N-vinyl pyrrolidone)-poly(ethylene glycol) hydrogels", Polym. Mater. Sci. Eng., vol. 81, pp. 456-457, (1999).
Chalykh et al., "Fracture mechanics of poly(N-vinyl pyrrolidone)-poly(ethylene glycol) hydrogel adhesive joints," Polym. Mater. Sci. Eng., vol. 81, pp. 427-428, (1999).
Chalykh et al., "Pressure-sensitive adhesion in the blends of poly(N-vinyl pyrrilidone) and poly(ethylene glycol) of disparate chain lengths," J. Adhesion, vol. 78, pp. 667-694, (2002).
Cleary et al., A new polymer blend adhesive with combined properties to adhere to either skin of mucosa for drug delivery, podium abstract, 30th annual Meeting and Exposition of the controlled Release Society, Glasgow, Scotland, Jul. 19-23, 2003, Abstract #123.
Database WPI Section Ch, Week 198451, Derwent Publications Ltd., London, GB: Class A96, AN 1984-315114 & JP 59196817 A (Sekisuki Chem Ind Co Ltd) Nov. 8, 1984 abstract.
Database WPI Section Ch, Week 199150, Derwent Publications Ltd., London GB: Class A18, AN 1991-366353 & JP 03247334 A (Sumitomo Rubber Ind Ltd) Nov. 5, 1991 abstract.
Database WPI Section Ch, Week 199118, Derwent Publications Ltd., London, GB: Class A96, AN 1991-128478 & JP 03066812 A (Sato Pharm Co Ltd) Mar. 22, 1991 abstract.
Database WPI Section Ch, Week 199627, Derwent Publications Ltd., London GB; Class A14, AN 1996-266746 & SU 1459215 A (A Med Cardiology Res Centre) Nov. 20, 1995 abstract.
Emla Cream, (lidocaine 2.5% and prilocaine 2.5%), EMLA Anesthetic Disc, (lidocaine 2.5% and prilocaine 2.5% cream), "Tropical anesthetic for dermal analgesia", AstraZeneca Product Monograph, 46 pgs, Revised May 25, 2010.
Feldstein et al., "A structure—property relationship and quantitative approach to the development of universal transdermal drug delivery system," NBC Risks, vol. 25, pp. 441-458, (1999).
Feldstein et al., "Coherence of thermal transitions in poly(N-vinyl pyrrolidone)—poly(ethylene glycol) compatible blends: 1. interrelations among the temperatures of melting, maximum cold crystalization rate and glass transitions", Polymer, vol. 41, pp. 5327-5338, (2000).
Feldstein et al., "Coherence of thermal transitions in poly(N-vinyl pyrrolidone)—poly(ehtylene glycol) compatible blends: 2. The temperature of maximum cold crystalization rate versus glass transitions", Polymer, vol. 41, pp. 5339-5348, (2000).
Feldstein et al., "Coherence of thermal transitions in poly(N-vinyl pyrrolidone)—poly(ethylene glycol) compatible blends: 3, Impact of sorbed water upon phase behavior", Polymer, vol. 41, pp. 5349-5359, (2000).
Feldstein et al., "Correlations between activation energy for debonding and that for self-diffusion in pressure-sensitive hydrogels", Proceed. 24th Annual Meeting Adhession Soc., pp. 137-140, (2001).
Feldstein et al., "Contribution of molecular mobility to debonding of pressure-sensitive adhesive hydrogels". Polym Mater. Sci. Eng., vol. 81, pp. 467-468, (1999).
Feldstein et al., "Effect of hydrophilic matric hydration on transdermal drug delivery kinetics: I. The matrix hydration In Vivo and In Vitro", Prediction of Percutaneous Penetration, vol. 4b, pp. 61-64, Brian, et al., (Eds.) (1996).
Feldstein et al., "Effect of hydrophilic matric hydration on transdermal drug delivery kinetics: II. In Vitro cytasine Delivery from Cypercuten TTS", Prediction of Percutaneous Penetration, vol. 4b, pp. 65-67, Brian, et al., (Eds.) (1996).
Feldstein et al., "Effect of hydrophilic matrix hydration on transdermal drug delivery kinetics: III. In Vitro clonide delivery from clopercuten TTS", Prediction of Percutaneous Penetration, vol. 4b, pp. 68-70, Brian, et al., (Eds.) (1996).
Feldstein et al., "Effect of hydrophillic matric hydration on transdermal drug delivery kinetics: IV, In Vitro—In Vivo correlation," Prediction of Percutaneous Penetration, vol. 4b, pp. 71-73, Brian, et al., (eds.) (1996).
Feldstein et al., "Effects of chains orientation, free volume and interaction on glass transition in poly(N-vinyl pyrrolidone)—poly(ethyl-

(56) References Cited

OTHER PUBLICATIONS ene glycol) blends involvong a stoichiometric hydrogen-B bonded network complex", Polym. Mater. Sci. Eng., vol. 82, pp. 365-366, (2000).
Feldstein et al., "General approach to the molecular design of hydrophilic pressure-sensitive adhesives," Proc. 25th Ann. Mtg. and 2nd World Congress on Adhesion and Related Phenomena, Orlando, FL. vol. 1, pp. 292-294 (2002).
Feldstein et al., "Molecular insight into rheological and diffusion determinants of pressure sensitive adhesion", Proceed 23rd Annual Meeting Adhesion Soc., pp. 54-56, (2000).
Feldstein et al., "Peculiarities of glass transition temperature relation to the composition of poly($N$-vinyl pyrolidone) blends with short chain poly(ethylene glycol)", Polymer, vol. 42, pp. 7719-7726, (2001).
Feldstein et al., "Quantitative relationship betweem molecular structure and adhesion of PVP-PEG hydrogels", Polym. Mater. Sci Eng., vol. 81, pp. 465-466, (1999).
Feldstein et al., "Relation of glass transition temperature to the hydrogen bonding degree and energy in poly($N$-vinyl pyrrolidone) blends with hydroxyl-containing plasticizers: 2. Effects of poly(ethylene gycol) chain length", Polymer, vol. 42, pp. 981-990, (2001).
Feldstein et al., "Universal hydrophilic drug-containing adhesive matrix for systemic and topical transdermal drug delivery", Proc. 1st World Meeting APGI/APV, Budapest, Sep. 2011, 2 pages, (1995).
Feldstein et al., "A new class of pressure-sensitive adhesives based on interpolymer and polymer-oligomer complexes", Polymer Science, vol. 51, No. 7, pp. 799-814 (2009).
Hnadbook of Pharmaceutical Excipients, Arther H. Kibbe, ed., 3rd ed., pp. 401-406, (2000).
Hawley's Condensed Chemical Dictionary, 14th Edition, Citation, "Oligomer, A polymer molecule of only a few monomer units (dimer, trimer, tetramer)", John Wiley and Sons, Inc., (2002).
International Search Report for PCT/US2000/018557 Mailed Oct. 17, 2000.
International Search Report for PCT/US2001/021417 Mailed Feb. 25, 2002.
International Search Report for PCT/US2002/013680 Mailed Sep. 18, 2002.
International Search Report for PCT/US2002/014260 Mailed Sep. 17, 2002.
International Search Report for PCT/US2002/014725 Mailed Sep. 27, 2002.
International Search Report for PCT/US2003/016408 Mailed Dec. 8, 2003.
International Search Report for PCT/US2003/039717 Mailed Jun. 28, 2004.
International Search Report for PCT/US2004/003443 Mailed Aug. 20, 2004.
International Search Report for PCT/US2004/011567 Mailed Jan. 10, 2006.
International Search Report for PCT/US2004/015448 Mailed Dec. 28, 2004.
International Search Report for PCT/US2004/029620 Mailed Jun. 1, 2005.
International Search Report for PCT/US2005/002873 Mailed Apr. 27, 2005.
International Search Report for PCT/US2005/034439 Mailed Jul. 19, 2006.
International Search Report for PCT/US2005/046577 Mailed Jul. 26, 2006.
International Search Report for PCT/US2005/028063 Mailed Apr. 28, 2006.
International Search Report for PCT/US2005/032525 Mailed Mar. 17, 2006.
International Search Report for PCT/US2006/000098 Mailed Nov. 3, 2006.
International Search Report for PCT/US2006/003091 Mailed Oct. 11, 2006.
International Search Report for PCT/US2006/018500 Mailed Sep. 21, 2006.
Kotomin et al., "Squeeze-recoil analysis of adhesive hydrogels and elastomers", Polym. Mater. Sci. Eng., vol. 81, pp. 425-426, (1999).
Kotomin et al., "Durability and fracture of some visceolastic adhesives," Proceed. of the 23rd Annual Meeting of the Adhesion Soc., pp. 413-415, (Feb. 20-23, 2000).
MSDS (Material Safety Data Sheet), Lactic Acid, No. L0522, (2008).
Patent Abstracts of Japan, vol. 017, No. 055 (C-I023) Feb. 3, 1993 & JP 04 266818 A (Sekisui Chem Co Ltd), Sep. 22, 1992 abstract.
Roos et al., "Probe tack investigation of poly(vinyl pyrrolidone)-poly(ethylene gylcol) blends", Proceed. 24th Annual Meeting Adhesion Soc., pp. 277-279, (2001).
Schehlmann "Polyvinylcaprolactam: physical and cosmetic properties of a new hair fixative resin", Lecture held at the IN-COSMETICS, SOFW-Journal-Sounderdruck, Dusseldorf, 6 pages (1997).
Sintov et al., "Radiofrequency-driven skin microchanneling as a new way for electically assisted transdermal delivery of hydrophilic drugs", J. Contr.Release, vol. 89, pp. 311-320, (2003).
Supplementary European Search Report for EP04783729.9 Mailed Jun. 5, 2009.
Vartapian et al., "Self-diffusion in poly($N$-vinyl pyrrolidone)-poly(ethylene glycol) systems", Colloid Polym. Sci., vol. 279, pp. 532-538, (2001).
Vartapian et al., "Molecular dynamics in poly($N$-vinyl pyrrolidone)-poly(ethylene gycol) blends by pulsed-field gradient NMR method: effects of aging, hydration and PEG chain length", Macromal. Chem. Phys., vol. 202, pp. 2648-2652, (2001).
Whelan Polymer Technology Dictionary, Citation Butyl Rubber, Chapman Hall, 2-6 Boundry Row, London, UK vol. 1, pp. 53 (1994).

HYDROGEL COMPOSITIONS WITH AN ERODIBLE BACKING MEMBER

CROSS-REFERENCE TO RELATED APPLICATIONS

This application is a continuation of U.S. patent application Ser. No. 13/482,965, filed May 29, 2012, now allowed, which is a continuation of U.S. patent application Ser. No. 10/661,103, filed Sep. 12, 2003, now issued as U.S. Pat. No. 8,206,738, which is a continuation in part of U.S. patent application Ser. No. 10/359,548, filed Feb. 5, 2003; which is a continuation in part of U.S. patent application Ser. No. 10/137,664, filed May 1, 2002; which claims priority under 35 U.S.C. §119(e)(1) to provisional U.S. Patent Application Ser. No. 60/288,008, filed May 1, 2001.

TECHNICAL FIELD

This invention relates generally to hydrogel compositions. More particularly the invention relates to hydrogel compositions useful as wound dressings and for administering a wide variety of active agents to mucosal tissue such as the mouth, including tooth whiteners. The assignees of this application, Corium International, Inc. and the A. V. Topchiev Institute of Petrochemical Synthesis, Russian Academy of Sciences, are parties to a joint research agreement covering work in this and other fields.

BACKGROUND

Discoloration of the teeth occurs widely in society, and is estimated to occur in two out of three adults. Dental discoloration is considered an aesthetic flaw or defect, and can have negative consequences in an affected person's life by causing self-consciousness, and even inhibiting smiling. Tooth discoloration can be particularly distressing or troublesome in situations and professions where showing clean and white teeth is essential.

A tooth is comprised of an inner dentin layer and an outer hard enamel layer that is slightly porous. The outer layer is the protective layer of the tooth. The natural color of the tooth is opaque to translucent white or slightly off-white. Staining of teeth arises as a result of exposure of compounds such as tannins and other polyphenolic compounds to the teeth. These compounds become trapped or bound to the proteinaceous layer on the surface of teeth, and can penetrate the enamel and even the dentin. On occasion, staining can arise from sources within the tooth, such as tetracycline, which may become deposited in the teeth if administered to an individual when young.

Surface staining can usually be removed by mechanical tooth cleaning. However, discolored enamel or dentin is not amenable to mechanical methods of tooth cleaning, and chemical methods, which can penetrate into the tooth structure, are required to remove the stains. The most effective treatments for dental discoloration are compositions containing an oxidizing agent, such as hydrogen peroxide, that is capable of reacting with the chromogen molecules responsible for the discoloration, and rendering them either colorless or water-soluble, or both.

Consequently, tooth whitening compositions generally fall into two categories: (1) gels, pastes, or liquids, including toothpastes that are mechanically agitated at the stained tooth surface in order to affect tooth stain removal through abrasive erosion of surface stains; and (2) gels, pastes, or liquids that accomplish a tooth-bleaching effect by a chemical process while in contact with the stained tooth surface for a specified period, after which the formulation is removed. In some cases, an auxiliary chemical process, which may be oxidative or enzymatic, supplements the mechanical process.

Some dental compositions such as dentrifices, toothpastes, gels, and powders contain active oxygen or hydrogen peroxide liberating bleaching agents. Such bleaching agents include peroxides, percarbonates and perborates of the alkali and alkaline earth metals or complex compounds containing hydrogen peroxide. Also, peroxide salts of the alkali or alkaline earth metals are known to be useful in whitening teeth.

Of the many peroxides available to the formulator of tooth whitening compositions, hydrogen peroxide (and its adducts or association complexes, such as carbamide peroxide and sodium percarbonate) has been used almost exclusively. The chemistry of hydrogen peroxide is well known, although the specific nature of its interactions with tooth chromogens is poorly understood. It is believed that hydrogen peroxide destroys tooth chromogens by oxidizing unsaturated carbon-carbon, carbon-oxygen, and carbon-nitrogen bonds found in the stain molecules, thus rendering them colorless or soluble.

A related class of compound, the peroxyacids, has been used in laundry detergents to effectively whiten clothes, due primarily to their stability in solution and their specific binding abilities to certain types of stain molecules. A number of stable, solid peroxyacids have been used, including diperoxydodecanoic acid and the magnesium salt of monoperoxyphthalic acid. Other peroxyacids, such as peroxyacetic acid, are available as solutions containing an equilibrium distribution of acetic acid, hydrogen peroxide, peroxyacetic acid and water. Alternatively, a peroxide donor such as sodium perborate or sodium percarbonate is formulated together with a peroxyacid precursor. Upon contact with water, the peroxide donor releases hydrogen peroxide which then reacts with the peroxyacid precursor to form the actual peroxyacid. Examples of peroxyacids created in situ include peroxyacetic acid (from hydrogen peroxide and tetraacetylethylenediamine) and peroxynonanoic acid (from hydrogen peroxide and nonanoyloxybenzene sulfonate).

Peroxyacids have also been used in oral care compositions to whiten stained teeth. U.S. Pat. No. 5,279,816 to Church et al. describes a method of whitening teeth comprising the application of a peroxyacetic acid-containing composition having an acid pH. EP 545,594 A1 to Church et al. describes the use of peroxyacetic acid in preparing a composition for whitening teeth. The peroxyacetic acid may be present in the composition, or alternatively, may be generated in situ by combining a peroxide source with a peroxyacetic acid precursor during use. For example, U.S. Pat. No. 5,302,375 to Viscio describes a composition that generates peroxyacetic acid within a vehicle in situ by combining water, acetylsalicylic acid and a waters-soluble alkali metal percarbonate.

The most commonly used dental whitening agent is carbamide peroxide $(CO(NH_2)_2H_2O_2)$, also called urea hydrogen peroxide, hydrogen peroxide carbamide, and perhydrol-urea. Carbamide peroxide had been used by dental clinicians for several decades as an oral antiseptic, and tooth bleaching was an observed side effect of extended contact time. Over-the-counter compositions of 10% carbamide peroxide are available as GLY-OXIDE® by Marion Laboratories and PROXIGEL® by Reed and Carnrick, which are low-viscosity compositions that must be held in a tray or similar container in order to provide contact with the teeth. A bleaching gel which is able to hold a comfortable-fitting dental tray in position for an extended time period is available under the trademark OPALESCENCE® from Ultradent Products, Inc. in South Jordan, Utah.

In order for such compositions to stay in place, the compositions must be a viscous liquid or a gel. The use of dental trays also requires that the tray be adapted for comfort and fit so that the tray will not exert pressure or cause irritation to the person's teeth or gums. Such whitening compositions necessarily should be formulated so as to be sufficiently sticky and viscous to resist dilution by saliva.

In one method of whitening an individual's teeth, a dental professional will construct a custom made dental bleaching tray for the patient from an impression made of the patient's dentition and prescribe the use of an oxidizing gel to be dispensed into the bleaching tray and worn intermittently for a period of from about 2 weeks to about 6 months, depending upon the severity of tooth staining. These oxidizing compositions, usually packaged in small plastic syringes or tubes, are dispensed directly by the patient into the custom-made tooth-bleaching tray, held in place in the mouth for contact times of greater than about 60 minutes, and sometimes as long as 8 to 12 hours. The slow rate of bleaching is in large part the consequence of the very nature of formulations that are developed to maintain stability of the oxidizing composition.

For example, U.S. Pat. No. 6,368,576 to Jensen describes tooth whitening compositions that are preferably used with a tray so that the composition is held in position adjacent to the person's tooth surfaces to be treated. These compositions are described as a sticky matrix material formed by combining a sufficient quantity of a tackifying agent, such as carboxypolymethylene, with a solvent, such as glycerin, polyethylene glycol, or water.

In another example, U.S. Pat. No. 5,718,886 to Pellico describes a tooth whitening composition in the form of a gel composition containing carbamide peroxide dispersed in an anhydrous gelatinous carrier, which includes a polyol, a thickener, and xanthan gum.

Yet another example is described in U.S. Pat. No. 6,419,905 to Hernandez, which describes the use of compositions containing carbamide peroxide (0.3-60%), xylitol (0.5-50%), a potassium salt (0.001-10%) and a fluorine salt (0.15-3%), formulated into a gel that contains between 0.5 and 6% by weight of an appropriate gelling agent.

A tooth whitening composition that adheres to the teeth is described in U.S. Pat. Nos. 5,989,569 and 6,045,811 to Dirksing. According to these patents, the gel contains 30-85% glycerin or polyethylene glycol, 10-22% urea/hydrogen peroxide complex, 0-12% carboxypolymethylene, 0-1% sodium hydroxide, 0-100% triethanolamine (TEA), 0-40% water, 0-1% flavor, 0-15% sodium citrate, and 0-5% ethylenediaminetetraacetic acid. The preferred gel according to Dirksing has a viscosity between 200 and 1,000,000 cps at low shear rates (less than one 1/seconds), and is sufficiently adhesive so as to obviate the need for a tray.

Currently available tooth-bleaching compositions have a significant disadvantage in that they cause tooth sensitization in over 50% of patients. Tooth sensitivity may result from the movement of fluid through the dentinal tubules, which is sensed by nerve endings in the tooth, due to the presence of glycerin, propylene glycol and polyethylene glycol in these compositions. This can result in varying amounts of tooth sensitivity following exposure of the teeth to heat, cold, overly sweet substances, and other causative agents.

Prolonged exposure of teeth to bleaching compositions, as practiced at present, has a number of adverse effects in addition to that of tooth sensitivity. These adverse effects include leaching of calcium from the enamel layer at a pH less than 5.5; penetration of the intact enamel and dentin by the bleaching agents and risking damage to pulpal tissue; and dilution of the bleaching compositions with saliva resulting in leaching from the dental tray and subsequent ingestion by the user.

Some oxidizing compositions (generally having relatively high concentrations of oxidizers) are applied directly to the tooth surface of a patient in a dental office setting under the supervision of a dentist or dental hygienist. Theoretically, such tooth whitening strategies yield faster results and better overall patient satisfaction. However, due to the high concentration of oxidizing agents contained in these so called "in-office" compositions, they can be hazardous to the patient and practitioner alike if not handled with care. The patient's soft tissues (the gingiva, lips, and other mucosal surfaces) must first be isolated from potential exposure to the active oxidizing agent by the use of a perforated rubber sheet (known as a rubber dam), so that only the teeth protrude. Alternatively, the soft tissue may be isolated from the oxidizers to be used in the whitening process by covering the soft tissue with a polymerizable composition that is shaped to conform to the gingival contours and subsequently cured by exposure to a high intensity light source. Once the soft tissue has been isolated and protected, the practitioner may apply the oxidizing agent directly onto the stained tooth surfaces for a specified period of time or until a sufficient change in tooth color has occurred. Typical results obtained through the use of an in-office tooth whitener, range from about 2 to 3 shades (as measured with the VITA Shade Guide, VITA Zahnfarbik).

The range of tooth shades in the VITA Shade Guide varies from very light (B1) to very dark (C4). A total of 16 tooth shades constitute the entire range of colors between these two endpoints on a scale of brightness. Patient satisfaction with a tooth whitening procedure increases with the number of tooth shade changes achieved, with a generally accepted minimum change desirable of about 4 to 5 VITA shades.

It is desirable, with respect to dental care products for tooth whitening, to provide dental care products utilizing an adhesive hydrogel that includes a whitening agent for removing stains from an individual's teeth. In addition, there is a constant need for the development of products to provide a protective dressing for mucosal surfaces or to provide delivery of active agents, for example transmucosal delivery of agents to mucosal tissue, tooth surface, gums, mucous membranes and other oral tissue. Compositions are desired that do not require the use of dental trays to provide contact between the active agent and the teeth or other oral surface. Such products ideally would cause minimal or no tooth sensitivity, would minimize or eliminate leakage of the active agent resulting in ingestion by the user or resulting in damage or irritation to the gums or mucous membranes of the mouth, would provide for longer wear duration, sustained dissolution of the active agent, improved efficacy, and be well tolerated by patients. It would also be desirable to provide a dental care product that is a solid composition and self-adhesive but which does not stick to the fingers of the user, or that is a non-solid (e.g., liquid or gel) and which forms a film when dry. Finally, current dental care products require that the system be worn for a specified length of time, e.g., 30 minutes, before being removed by the user. It is desirable to develop products which can self-erode after the active has been released or the desired therapeutic or cosmetic effect has been achieved, since such systems would improve patient compliance. The instant invention addresses these needs.

SUMMARY OF THE INVENTION

One aspect of the invention relates to a hydrogel composition comprising a water-swellable, water-insoluble polymer, a blend of a hydrophilic polymer with a complementary oligomer capable of hydrogen bonding or electrostatic bonding to the hydrophilic polymer. An active agent such as a tooth whitening agent may also be included. The composition further comprises a backing member that erodes in a moist environment at a slower rate than the hydrogel. The hydrogel can be solid and the backing member attached to the backing member prior to use. The hydrogel can also be a non-solid and attached to the backing member during use.

In a preferred embodiment, the water-swellable, water-insoluble polymer is a cellulose ester, or an acrylate polymer; the hydrophilic polymer is an poly(N-vinyl lactam), poly(N-vinyl amide), poly(N-alkylacrylamide), or copolymer and blend thereof; and the complementary oligomer capable of hydrogen or electrostatic bonding to the hydrophilic polymer is a polyhydric alcohol, polyalkylene glycol or a carboxyl-terminated polyalkylene glycol. A preferred active agent is a whitening agent such as a peroxide.

The composition optionally comprises a low molecular weight plasticizer, and may also comprise at least one additive selected from the group consisting of fillers, preservatives, pH regulators, softeners, thickeners, colorants (e.g., pigments, dyes, refractive particles, etc.), flavorants (e.g., sweeteners, flavors), stabilizers, surfactants, toughening agents and detackifiers.

In a preferred method of using the composition, the composition is a tooth whitening composition and is applied to the teeth in need of whitening, and then removed when the degree of whitening has been achieved. In certain embodiments, the tooth whitening composition is translucent, and the composition is removed when the user is satisfied with the degree of whitening achieved.

Yet another aspect of the invention pertains to a composition comprising a water-swellable, water-insoluble polymer, a blend of a hydrophilic polymer with a complementary oligomer capable of hydrogen or electrostatic bonding to the hydrophilic polymer, and an active agent. In one aspect the active agent is selected from the group consisting of peroxides, metal chlorites, perborates, percarbonates, peroxyacids, and combinations thereof. The composition further comprises a backing member that erodes at a slower rate than the hydrogel.

Another aspect of the invention relates to a method for preparing a hydrogel film suitable for incorporation into an oral care or transmucosal composition is provided. This method comprises preparing a solution or a gel of a water-swellable, water-insoluble polymer, a hydrophilic polymer, and a complementary oligomer capable of hydrogen bonding or electrostatic bonding to the hydrophilic polymer, in a solvent; depositing a layer of the solution on a substrate to provide a coating thereon; and heating the coated substrate to a temperature in the range of about 80° C. to about 100° C. for a time period in the range of about 1 to about 4 hours, thereby providing a hydrogel film on the substrate.

In another method of forming a composition of the invention, the method comprises melt processing through an extruder a mixture of a water-swellable, water-insoluble polymer, a hydrophilic polymer, and a complementary oligomer capable of hydrogen bonding or electrostatic bonding to the hydrophilic polymer, to form an extruded composition; wherein the composition is extruded as a film of desired thickness onto a suitable substrate. The substrate can be an erodible backing member or the composition can be later pressed onto or laminated to an erodible backing member. The method further comprises loading the hydrogel film with an active agent such as a whitening agent, thereby providing a tooth whitening composition.

The adhesive compositions of the invention provide a number of significant advantages relative to the prior art. In particular, the present compositions provide one or more of the following advantages over the art:

(1) provide ease of handling;

(2) are readily modified during manufacture so that properties such as adhesion, absorption, translucence, and swelling can be controlled and optimized;

(3) can be formulated so that tack increases or decreases in the presence of moisture so that the composition is not sticky until moistened;

(4) minimize leakage of the active agent, when included, from the composition onto a mucosal surface (e.g., into the user's mouth);

(5) can be fabricated in translucent from, enabling the user to view the extent of whitening without removing the hydrogel composition from the teeth or mucosal surface;

(6) minimize damage to gums or mucous membranes in the mouth;

(7) can be worn comfortably and unobtrusively;

(8) are easily removed from the teeth or mucosal surface, and leave no residue;

(9) are amenable to extended duration of wear or action;

(10) can provide sustained and controlled release of a variety of active agents;

(11) can be formulated to erode after predetermined time; and

(12) can be formulated to deliver active agents uni-directionally, e.g., only towards the mucosal tissue, or bi-directionally, e.g., towards the mucosal surface as well as towards the oral cavity, and the relative rates of delivery towards the mucosal surface and the oral cavity are controlled by selecting a backing member having a predetermined permeability.

DETAILED DESCRIPTION OF THE INVENTION

I. Definitions and Nomenclature

Before describing the present invention in detail, it is to be understood that unless otherwise indicated this invention is not limited to specific hydrogel materials or manufacturing processes, as such may vary. It is also to be understood that the terminology used herein is for the purpose of describing particular embodiments only, and is not intended to be limiting. It must be noted that, as used in this specification and the appended claims, the singular forms "a," "an," and "the" include plural referents unless the context clearly dictates otherwise. Thus, for example, reference to "a hydrophilic polymer" includes not only a single hydrophilic polymer but also a combination or mixture of two or more different hydrophilic polymers, reference to "a plasticizer" includes a combination or mixture of two or more different plasticizers as well as a single plasticizer, and the like.

In describing and claiming the present invention, the following terminology will be used in accordance with the definitions set out below.

The definitions of "hydrophobic" and "hydrophilic" polymers are based on the amount of water vapor absorbed by polymers at 100% relative humidity. According to this classification, hydrophobic polymers absorb only up to 1 wt % water at 100% relative humidity ("rh"), while moderately hydrophilic polymers absorb 1-10% wt % water, hydrophilic polymers are capable of absorbing more than 10 wt % of water, and hygroscopic polymers absorb more than 20 wt % of water. A "water-swellable" polymer is one that absorbs an amount of water greater than at least 25 wt % of its own weight, and preferably at least 50 wt % of its own weight, upon immersion in an aqueous medium.

The term "crosslinked" herein refers to a composition containing intramolecular and/or intermolecular crosslinks, whether arising through covalent or noncovalent bonding. "Noncovalent" bonding includes both hydrogen bonding and electrostatic (ionic) bonding.

The term "polymer" includes linear and branched polymer structures, and also encompasses crosslinked polymers as well as copolymers (which mayor may not be crosslinked), thus including block copolymers, alternating copolymers, random copolymers, and the like. Those compounds referred to herein as "oligomers" are polymers having a molecular weight below about 1000 Da, preferably below about 800 Da.

The term "hydrogel" is used in the conventional sense to refer to water-swellable polymeric matrices that can absorb a substantial amount of water to form elastic gels, wherein "matrices" are three-dimensional networks of macromolecules held together by covalent or noncovalent crosslinks Upon placement in an aqueous environment, dry hydrogels swell to the extent allowed by the degree of cross-linking Hydrogels are also erodible.

The term "erodes" as in "the hydrogel erodes" or "erodible" as in "an erodible backing member" is intended to include the processes of erosion, dissolution, disintegration, and degradation, as well as to include those materials that are often referred to as being bioerodible or biodegradable. Irrespective of the mechanism by which the hydrogel and backing member dissipate in a moist environment, the components of the backing member are preferably selected so that the backing member "erodes" at a slower rate than the hydrogel components.

The terms "active agent," "pharmacologically active agent" and "drug" are used interchangeably herein to refer to a chemical material or compound that induces a desired pharmacological, physiological effect, and include agents that are therapeutically effective, prophylactically effective, or cosmeceutically effective. The terms also encompass pharmaceutically acceptable, pharmacologically active derivatives and analogs of those active agents specifically mentioned herein, including, but not limited to, salts, esters, amides, prodrugs, active metabolites, inclusion complexes, analogs, and the like. When the terms "active agent," "pharmacologically active agent" and "drug" are used, it is to be understood that both the active agent per se as well as pharmaceutically acceptable, pharmacologically active salts, esters, amides, prodrugs, active metabolites, inclusion complexes, analogs, etc., are included.

The term "tooth whitening composition" refers to a composition that contains a hydrogel, as defined herein, and a whitening agent.

The term "whitening agent" typically refers to an oxidizing agent such as a peroxide or a chlorite, as will be discussed in greater detail below. In some instances, the whitening agent may be an enzyme or other catalytic means for removing a stain from the teeth. The whitening agent may include one or more additional whitening agents, surfactants, antiplaque agents, antitartar agents and abrasive agents. The whitening agent may have additional therapeutic benefits.

The term "effective amount" or "a cosmeceutically effective amount" of a cosmeceutically active agent is meant a nontoxic but sufficient amount of a cosmeceutically active agent to provide the desired cosmetic effect. The term "effective amount" or "a therapeutically effective amount" of a drug or pharmacologically active agent is intended to mean a nontoxic but sufficient amount of the drug or agent to provide the desired therapeutic effect. The amount that is "effective" will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation. Furthermore, the exact "effective" amount of an active agent incorporated into a composition or dosage form of the invention is not critical, so long as the concentration is within a range sufficient to permit ready application of the formulation so as to deliver an amount of the active agent that is within a therapeutically effective range.

The term "surface" as in "oral cavity" surface or "body surface" is intended to include mucosal body surfaces (e.g., sublingual, buccal, vaginal, rectal, urethral), as well as surfaces in and around the oral cavity (e.g., teeth, lips, gums, mucous membranes). These surfaces are typically located in what is referred to herein as a "moist" environment.

"Transmucosal" drug delivery is meant administration of a drug to the mucosal tissue surface of an individual so that the drug passes through the mucosal tissue (e.g., sublingual, buccal, vaginal, rectal, urethral) and into the individual's blood stream, thereby providing a systemic effect. The term "transmucosal" is intended to cover both local and systemic effects, and therefore includes topical administration, i.e., delivery of a topical agent to the mucosa, as in, for example, the treatment of various mucosal tissue disorders to provide a local effect.

The terms "tack" and "tacky" are qualitative. However, the terms "substantially nontacky" "slightly tacky" and "tacky," as used herein, may be quantified using the values obtained in a PKI or TRBT tack determination method, as follows. By "substantially nontacky" is meant a hydrogel composition that has a tack value that is less than about 25 g-cm/sec, by "slightly tacky" is meant a hydrogel composition that has a tack value in the range of about 25 g-cm/sec to about 100 g-cm/sec, and by "tack" is meant a hydrogel composition that has a tack value of at least 100 g-cm/sec.

The term "water-insoluble" refers to a compound or composition whose solubility in water is less than 5 wt %, preferably less than 3 wt %, more preferably less than 1 wt % (measured in water at 20° C.).

The term "translucent" is used herein to signify a material capable of transmitting light so that objects or images can be seen through the material. Translucent materials herein mayor may not be "transparent," meaning that the material is optically clear. The term "translucent" indicates that a material is not "opaque," in which case objects and images cannot be seen through the material.

II. Hydrogel Compositions

The composition of the invention is a single phase hydrogel comprised of a water-swellable, water-insoluble polymer, and a blend of a hydrophilic polymer with a complementary oligomer, and an optional active agent such as a whitening agent. Both the water-swellable, water-insoluble polymer and the oligomer may be capable of hydrogen or electrostatic bonding to the hydrophilic polymer.

The composition also includes a backing member comprised of a polymer composition that erodes in the moist environment at a slower rate than the hydrogel.

The water-swellable, water-insoluble polymer, i.e., a polymer that is capable of swelling when immersed in an aqueous liquid but that is insoluble in water within a selected pH range (generally less than pH 5.5), is a cellulose ester, alginic acid, or an acrylate polymer. The term "acrylate polymer" is intended to include acrylate and acrylate-based polymers and copolymers, and is an acrylic acid or acrylic acid ester polymer. The polymer generally swells by at least 25 wt %, and preferably by at least 50 wt % of its own weight when immersed in water or aqueous solution. In some embodiments utilizing certain hydrophilic polymers, the composition may swell by as much as 1400 wt % of its dry weight.

In one embodiment, the composition is a tooth whitening composition, where the whitening agent functions to whiten the tooth surface to which the composition is applied. However, the whitening agent may have other utilities, for example as a therapeutic agent or other type of cosmeceutical agent, e.g., for skin lightening. Therefore, the compositions described herein may find utility as pharmaceutical compositions to be applied to a body surface (e.g., teeth, nails, skin, mucosa, etc.) for the treatment of a disease state. For example, hydrogen peroxide also has antibiotic and anti-acne properties, as well as being a whitening agent. Therefore, the invention also contemplates treating an infection or acne by applying a hydrogen peroxide-containing composition of the invention to a body surface. Other diseases states include, by way of illustration and not limitation, fungal infections, acne, wounds, skin lightening, and so forth. In addition, a number of active agents can be incorporated in the composition of the invention to treat a variety of diseases that affect the oral cavity.

A. Water-Swellable, Water-Insoluble Polymers

For solid compositions, the water-swellable, water-insoluble polymer represents about 1-20 wt %, preferably about 6-12 wt % of the composition; the hydrophilic polymer represents about 20-80 wt %, preferably about 40-60 wt % of the composition; the complementary oligomer represents about 10-50 wt %, preferably about 15-35 wt % of the composition; and the active agent, when present, represents about 0.1-60 wt %, preferably about 1-30 wt % of the composition. Optimally, the complementary oligomer represents about 10-80 wt %, preferably about 20-50 wt % of the hydrophilic polymer/complementary oligomer blend.

For non-solid compositions, the water-swellable, water-insoluble polymer represents about 0.1-20 wt %, preferably about 2-6 wt % of the composition; the hydrophilic polymer represents about 1-40 wt %, preferably about 4-10 wt % of the composition; the complementary oligomer represents about 0.1-20 wt %, preferably about 0.5-10 wt % of the composition; and the active agent, when present, represents about 0.1-60 wt %, preferably about 1-40 wt % of the composition. Optimally, the complementary oligomer represents about 1-85 wt %, preferably about 5-50 wt % of the hydrophilic polymer/complementary oligomer blend.

The adhesion profile can be tailored based on type of polymer, the composition ratio and the extent of water in the blend. The water-swellable, water-insoluble polymer is selected so as to provide the desired adhesion profile with respect to hydration. That is, when the water-swellable, water-insoluble polymer is a cellulose ester, the composition is generally tacky prior to contact with water (e.g., with a moist surface) but gradually loses tack as the composition absorbs moisture. When the water-swell able, water-insoluble polymer is an acrylate polymer or copolymer, a composition is provided that is generally substantially nontacky prior to contact with water, but becomes tacky upon contact with a moist surface.

The water-swellable, water-insoluble polymer is capable of at least some degree of swelling when immersed in an aqueous liquid but is insoluble in water. The hydrophilic polymer may function to help solubilize the water-insoluble polymer. The polymer may be comprised of a cellulose ester, for example, cellulose acetate, cellulose acetate propionate (CAP), cellulose acetate butyrate (CAB), cellulose propionate (CP), cellulose butyrate (CB), cellulose propionate butyrate (CPB), cellulose diacetate (CDA), cellulose triacetate (CTA), or the like. These cellulose esters are described in U.S. Pat. Nos. 1,698,049; 1,683,347; 1,880,808; 1,880,560; 1,984,147; 2,129,052; and 3,617,201, and may be prepared using techniques known in the art or obtained commercially. Commercially available cellulose esters suitable herein include CA 320, CA 398, CAB 381, CAB 551, CAB 553, CAP 482, CAP 504, all available from Eastman Chemical Company, Kingsport, Tenn. Such cellulose esters typically have a number average molecular weight of between about 10,000 and about 75,000.

Generally, the cellulose ester comprises a mixture of cellulose and cellulose ester monomer units; for example, commercially available cellulose acetate butyrate contains cellulose acetate monomer units as well as cellulose butyrate monomer units and unesterified cellulose monomer units, while cellulose acetate proprionate contains monomer units such as cellulose proprionate. Preferred cellulose esters herein are cellulose acetate propionate compositions and cellulose acetate butyrate compositions having the butyryl, propionyl, acetyl, and unesterified (OH) cellulose content as indicated below:

|  |  | Acetyl (%) | OH (%) | MW (g/mole) | $T_g$ (° C.) | $T_m$ (° C.) |
| --- | --- | --- | --- | --- | --- | --- |
| Cellulose Acetate Butyrate | 17-52% Butyrate | 2.0-29.5 | 1.1-4.8 | 12,000-70,000 | 96-141 | 130-240 |
| Cellulose Acetate Propionate | 42.5-47.7% Propionate | 0.6-1.5 | 1.7-5.0 | 15,000-75,000 | 142-159 | 188-210 |

The preferred molecular weight, glass transition temperature ($T_g$) and melting temperature ($T_m$) are indicated. Also, suitable cellulosic polymers typically have an inherent viscosity (I.V.) of about 0.2 to about 3.0 deciliters/gram, preferably about 1 to about 1.6 deciliters/gram, as measured at a temperature of 25° C. for a 0.5 gram sample in 100 ml of a 60/40 by weight solution of phenol/tetrachloroethane. When prepared using a solvent casting technique, the water-swellable, water-insoluble polymer should be selected to provide greater cohesive strength and thus facilitate film forming (generally, for example, cellulose acetate propionate tends to improve cohesive strength to a greater degree than cellulose acetate butyrate).

Other preferred water-swellable polymers are acrylate polymers, generally formed from acrylic acid, methacrylic acid, methyl acrylate, ethyl acrylate, methyl methacrylate, ethyl methacrylate, and/or other vinyl monomers. Suitable acrylate polymers are those copolymers available under the tradename "Eudragit" from Rohm Pharma (Germany). The Eudragit® series E, L, S, RL, RS and NE copolymers are available solubilized in organic solvent, in an aqueous dispersion, or as a dry powder. Preferred acrylate polymers are copolymers of methacrylic acid and methyl methacrylate, such as the Eudragit L and Eudragit S series polymers. Particularly preferred such copolymers are Eudragit L 30D-55 and Eudragit L 100-55 (the latter copolymer is a spray-dried form of Eudragit L 30D-55 that can be reconstituted with water). The molecular weight of the Eudragit L 30D-55 and Eudragit L 100-55 copolymer is approximately 135,000 Da, with a ratio of free carboxyl groups to ester groups of approximately 1:1. The Eudragit L 100-55 copolymer is generally insoluble in aqueous fluids having a pH below 5.5. Another particularly suitable methacrylic acid-methyl methacrylate copolymer is Eudragit S-100, which differs from Eudragit L 30D-55 in that the ratio of free carboxyl groups to ester groups is approximately 1:2. Eudragit S-100 is insoluble at pH below 5.5, but unlike Eudragit L 30D-55, is poorly soluble in aqueous fluids having a pH in the range of 5.5 to 7.0. This copolymer is soluble at pH 7.0 and above. Eudragit L 100 may also be used, which has a pH-dependent solubility profile between that of Eudragit L 30D-55 and Eudragit S-100, insofar as it is insoluble at a pH below 6.0. It will be appreciated by those skilled in the art that Eudragit L 30D-55, L 100-55, L 100, and S 100 can be replaced with other acceptable polymers having similar pH-dependent solubility characteristics. Other suitable acrylate polymers are those methacrylic acid/ethyl acrylate copolymers available under the tradename "Kollicoat" from BASF AG (Germany). For example, Kollicoat MAE has the same molecular structure as Eudragit L 100-55.

When the water-swellable polymer is an acrylic acid or acrylate polymer, a hydrogel is provided that can be reversibly dried, i.e., after removal of water and any other solvents, the dried hydrogel may be reconstituted to its original state by addition of water. In addition, hydrophilic hydrogels prepared with an acrylic acid/acrylate water-swellable polymer are generally substantially nontacky prior to contact with water, but become tacky upon contact with a moist surface, such as is found in the interior of the mouth, such as on the surface of the teeth. This property of being nontacky prior to contact with water enables positioning or repositioning on a chosen surface before, or as the hydrogel becomes tacky. Once hydrated, the hydrogel becomes tacky and adheres to the surface of the teeth or mucosal surface.

In addition, acrylate-containing compositions can generally provide swelling in the range of about 400% to 1500% upon immersion of the hydrogel composition in water or other aqueous liquid, at a pH of less than 5.5, although the ratio of the acrylate polymer to the hydrophilic polymer/complementary oligomer blend can be selected such that the rate and extent of swelling in an aqueous environment has a predetermined pH-dependence. This feature also provides for retroactive incorporation of whitening agents or other active agents, such as loading the composition with peroxide, peroxy acids, chlorites, stabilizers, flavoring agents, etc.

By contrast, incorporating a cellulose ester as the water-swellable polymer renders the hydrogel tacky prior to application to a moist surface, but nontacky upon absorption of water. It will be appreciated that such a composition may be desirable when a decrease in tack is desired for ultimate removal of the product from the teeth.

Another suitable water-swellable, water-insoluble polymer is alginic acid, which is insoluble in water at pH values below 5.5, but is capable of absorbing water and swelling.

B. Hydrophilic Polymers

The second component of the hydrogel composition is a blend of a hydrophilic polymer with a complementary oligomer capable of hydrogen bonding or electrostatic bonding to the hydrophilic polymer. Referring to this as a "blend" is intended to mean that the interaction of the hydrophilic polymer and the oligomer dominate the hydrogel properties. However, the addition of the water-swellable, water-insoluble polymer, serves to tailor the properties of this blend so as to obtain a single phase hydrogel with the desired characteristics. Such tailoring can be accomplished by selection of a particular water-swellable, water-insoluble polymer, or the inclusion of a certain amount of polymer, or even by the timing of the addition of the polymer to the other ingredients (hydrophilic polymer, complementary oligomer, active agent, etc.) during manufacture.

The hydrophilic polymer is generally a relatively high molecular weight polymer, and the complementary oligomer is generally a lower molecular weight polymer. For solid compositions, the water-swellable, water-insoluble polymer represents about 1-20 wt %, preferably about 6-12 wt % of the composition; the hydrophilic polymer represents about 20-80 wt %, preferably about 40-60 wt % of the composition; the complementary oligomer represents about 10-50 wt %, preferably about 15-35 wt % of the composition; and the whitening agent represents about 0.1-60 wt %, preferably about 1-30 wt % of the composition. Optimally, the complementary oligomer represents about 10-80 wt %, preferably about 20-50 wt % of the hydrophilic polymer/complementary oligomer blend.

Suitable hydrophilic polymers include repeating units derived from an N-vinyl lactam monomer, a carboxy vinyl monomer, a vinyl ester monomer, an ester of a carboxy vinyl monomer, a vinyl amide monomer, and/or a hydroxy vinyl monomer. Such polymers include, by way of example, poly (N-vinyl lactams), poly(N-vinyl acrylamides), poly(N-alkylacrylamides), substituted and unsubstituted acrylic and methacrylic acid polymers (e.g., polyacrylic acids and polymethacrylic acids), polyvinyl alcohol (PVA), polyvinylamine, copolymers thereof and copolymers with other types of hydrophilic monomers (e.g. vinyl acetate).

Poly(N-vinyl lactams) useful herein are preferably non-crosslinked homopolymers or copolymers of N-vinyl lactam monomer units, with N-vinyl lactam monomer units representing the majority of the total monomeric units of a poly (N-vinyl lactams) copolymer. Preferred poly(N-vinyl lactams) for use in conjunction with the invention are prepared by polymerization of one or more of the following N-vinyl lactam monomers: N-vinyl-2-pyrrolidone; N-vinyl-2-valero-lactam; and N-vinyl-2-caprolactam. Nonlimiting examples of non-N-vinyl lactam comonomers useful with N-vinyl lactam monomeric units include N,N-dimethylacrylamide, acrylic acid, methacrylic acid, hydroxyethylmethacrylate, acrylamide, 2-acrylamido-2-methyl-1-propane sulfonic acid or its salt, and vinyl acetate.

Poly (N-alkylacrylamides) include, by way of example, poly(methacrylamide) and poly(N-isopropyl acrylamide) (PNIPAM).

Polymers of carboxy vinyl monomers are typically formed from acrylic acid, methacrylic acid, crotonic acid, isocrotonic acid, itaconic acid and anhydride, a 1,2-dicarboxylic acid such as maleic acid or fumaric acid, maleic anhydride, or mixtures thereof, with preferred hydrophilic polymers within this class including polyacrylic acid and polymethacrylic acid, with polyacrylic acid most preferred.

Preferred hydrophilic polymers herein are the following: poly(N-vinyl lactams), particularly polyvinyl pyrrolidone (PVP) and polyvinyl caprolactam (PVCap); poly(N-vinyl acetamides), particularly polyacetamide per se; polymers of carboxy vinyl monomers, particularly polyacrylic acid and polymethacrylic acid; and copolymers and blends thereof. PVP and PVCap are particularly preferred.

The molecular weight of the hydrophilic polymer is not critical; however, the number average molecular weight of the hydrophilic polymer is generally in the range of approximately 100,000 to 2,000,000, more typically in the range of approximately 500,000 to 1,500,000. The oligomer is "complementary" to the hydrophilic polymers in that it is capable of hydrogen or electrostatic bonding, thereto. Preferably, the complementary oligomer is terminated with hydroxyl groups, amino or carboxyl groups. The oligomer typically has a glass transition temperature $T_g$ in the range of about $-100°$ C. to about $-30°$ C. and a melting temperature $T_m$ lower than about $20°$ C. The oligomer may be also amorphous. The difference between the $T_g$ values of the hydrophilic polymer and the oligomer is preferably greater than about $50°$ C., more preferably greater than about $100°$ C., and most preferably in the range of about $150°$ C. to about $300°$ C. The hydrophilic polymer and complementary oligomer should be compatible, i.e. capable of forming a homogeneous blend.

C. Complementary Oligomer

As noted above, the complementary oligomer is capable of hydrogen or electrostatic bonding to the hydrophilic polymer. The complementary oligomer may be capable of covalently bonding to the hydrophilic polymer as well. In addition, the complementary oligomer may be capable of hydrogen or electrostatic bonding to the water-swellable, water-insoluble polymer.

Generally, the complementary oligomer will have a molecular weight in the range from about 45 to about 800, preferably in the range of about 45 to about 600. The complementary oligomer is preferably a low molecular weight polyalkylene glycol (molecular weight 200-600) such as polyethylene glycol 400, which can also serve as a low molecular weight plasticizer. Alternatively, a different compound can be incorporated as an additional low molecular weight plasticizer, in which case any of the low molecular weight plasticizers described below can be used. In one embodiment of the invention, the complementary oligomers is a complementary low molecular weight or oligomeric plasticizer that contains at least two functional groups per molecule that are capable of hydrogen or electrostatic bonding to the hydrophilic polymer.

In some instances, the complementary oligomer may also serve as a low molecular weight plasticizer. Alternatively, a different compound can be incorporated as an additional low molecular weight plasticizer and, if included, would be present as approximately 30 to 35 wt % of the composition.

Examples of suitable complementary oligomers include, but are not limited to, low molecular weight polyhydric alcohols (e.g. glycerol or sorbitol), monomeric and oligoalkylene glycols such as ethylene glycol and propylene glycol, ether alcohols (e.g., glycol ethers), carbonic diacids, alkane diols from butane diol to octane diol, including carboxyl-terminated and amino-terminated derivatives of polyalkylene glycols. Polyalkylene glycols, optionally carboxyl-terminated, are preferred herein, and polyethylene glycol having a molecular weight in the range of about 200 to 600 is an optimal complementary oligomer.

It will be appreciated from the foregoing that a single compound, e.g., a low molecular weight polyalkylene glycol such as polyethylene glycol having a molecular weight in the range of about 200 to 600, can serve as both the complementary oligomer and the low molecular weight plasticizer.

As discussed in U.S. Patent Publication No. 2002/0037977 to Feldstein et al., the ratio of the hydrophilic polymer to the complementary oligomer in the aforementioned blend affects both adhesive strength and the cohesive strength. As explained in the aforementioned patent application, the complementary oligomer decreases the glass transition of the hydrophilic polymer/complementary oligomer blend to a greater degree than predicted by the Fox equation, which is given by equation (1)

$$\frac{1}{T_{g\ predicted}} = \frac{w_{pol}}{T_{g\ pol}} + \frac{w_{pl}}{T_{g\ pl}} \qquad (1)$$

where $T_{g\ predicted}$ is the predicted glass transition temperature of the hydrophilic polymer/complementary oligomer blend, $w_{pol}$ is the weight fraction of the hydrophilic polymer in the blend, $w_{pl}$ is the weight fraction of the complementary oligomer in the blend, $T_{g\ pol}$ is the glass transition temperature of the hydrophilic polymer, and $T_{g\ pl}$ is the glass transition temperature of the complementary oligomer. As also explained in that patent application, an adhesive composition having optimized adhesive and cohesive strength can be prepared from a hydrophilic polymer with a complementary oligomer by selecting the components and their relative amounts to give a predetermined deviation from $T_{g\ predicted}$. Generally, to maximize adhesion, the predetermined deviation from $T_{g\ predicted}$ will be the maximum negative deviation, while to minimize adhesion, any negative deviation from $T_{g\ predicted}$ is minimized.

As the complementary oligomer may itself act as a plasticizer, it is not generally necessary to incorporate an added plasticizer. However, inclusion of an additional low molecular weight plasticizer in the composition is optional and may, in some cases, be advantageous. Suitable low molecular weight plasticizers include: dialkyl phthalates, dicycloalkyl phthalates, diaryl phthalates, and mixed alkyl-aryl phthalates, as represented by dimethyl phthalate, diethyl phthalate, dipropyl phthalate, di(2-ethylhexyl)-phthalate, di-isopropyl phthalate, diamyl phthalate and dicapryl phthalate; alkyl and aryl phosphates such as tributyl phosphate, trioctyl phosphate, tricresyl phosphate, and triphenyl phosphate; alkyl citrate and citrate esters such as trim ethyl citrate, triethyl citrate, tributyl citrate, acetyl triethyl citrate, and trihexyl citrate; dialkyl adipates such as dioctyl adipate (DOA); also referred to as bis(2-ethylhexyl)adipate), diethyl adipate, di(2-methylethyl)adipate, and dihexyl adipate; dialkyl tartrates such as diethyl tartrate and dibutyl tartrate; dialkyl sebacates such as diethyl sebacate, dipropyl sebacate and dinonyl sebacate; dialkyl succinates such as diethyl succinate and dibutyl succinate; alkyl glycolates, alkyl glycerolates, glycol esters and glycerol esters such as glycerol diacetate, glycerol triacetate (triacetin), glycerol monolactate diacetate, methyl phthalyl ethyl glycolate, butyl phthalyl butyl glycolate, ethylene glycol diacetate, ethylene glycol dibutyrate, triethylene glycol diacetate, triethylene glycol dibutyrate and triethylene glycol dipropionate; and mixtures thereof. Preferred low molecular weight plasticizers for the continuous hydrophilic phase are triethyl citrate, tributyl citrate, diethyl phthalate, and dioctyl adipate, with dioctyl adipate most preferred.

The properties of the composition of the invention are readily controlled by adjusting one or more parameters during fabrication. For example, the adhesive strength of the composition can be controlled during manufacture in order to increase, decrease, or eliminate adhesion. This can be accomplished by varying type and/or amount of different components, or by changing the mode of manufacture. Also, with respect to the fabrication process, compositions prepared using a conventional melt extrusion process are generally, although not necessarily, somewhat less tacky than compositions prepared using a solution cast technique. Furthermore, the degree to which the hydrogel composition will swell upon contact with water can be varied by selecting different water-swellable polymers, and, in those compositions containing a continuous hydrophilic phase, by adjusting the ratio of the water-swellable, water-insoluble polymer to the hydrophilic polymer/complementary plasticizer blend. These compositions may vary in appearance from clear, transparent to translucent to opaque. In addition, certain compositions may be rendered translucent by changing the relative quantities of the components in the hydrophilic phase (e.g., by decreasing the amount of the cellulose ester), or by changing the fabrication method (translucent hydro gels are more readily obtained using solution casting than melt extrusion). In this manner, the translucent composition allows the user to observe the therapeutic or cosmetic (e.g., whitening) process while it is occurring and determine when the desired effect has been obtains, for example when the teeth have been sufficiently whitened.

D. Active Agents

The composition can also include any pharmaceutically active agent useful in treating physiological conditions involving the teeth, and surrounding tissue, as well as other mucosal tissues. The active agent can be any substance that can be released from the composition to treat an undesirable physiological condition. Undesirable, physiological conditions involving the teeth or surrounding tissue which are amenable to treatment with the present device include: halitosis; periodontal and oral infections; periodontal lesions; dental caries or decay; gingivitis; and other periodontal diseases. The active agent can be present in the hydrogel and/or the backing member. Furthermore, several agents can be incorporated into the composition of the invention. For example, the hydrogel may contain a tooth whitening agent that is released onto a tooth surface, while the backing can be loaded with a different active such as a breath freshener, which is released to oral cavity.

Such agents would be present in a cosmeceutically or therapeutically effective amount. These include, by way of example and not limitation, adrenergic agents, adrenocortical steroids, adrenocortical suppressants, alcohol deterrents, aldosterone antagonists, amino acids, ammonia detoxicants, anabolic agents, analeptic agents, analgesic agents, androgenic agents, anesthetic agents, anorectic compounds, anorexic agents, antagonists, anterior pituitary activators and anterior pituitary suppressants, anthelmintic agents, anti-acne agents, anti-adrenergic agents, anti-allergic agents, anti-amebic agents, anti-androgen agents, anti-anemic agents, anti-anginal agents, anti-anxiety agents, anti-arthritic agents, anti-asthmatic agents, anti-atherosclerotic agents, antibacterial agents, anticholelithic agents, anticholelithogenic agents, anticholinergic agents, anticoagulants, anticoccidal agents, anticonvulsants, antidepressants, antidiabetic agents, antidiarrheal agents, antidiuretics, antidotes, antidyskinetics agents, anti-emetic agents, antiepileptic agents, anti-estrogen agents, anti fibrinolytic agents, antifungal agents, antiglaucoma agents, antihemophilic agents, antihemophilic Factor, antihemorrhagic agents, antihistaminic agents, antihyperlipidemic agents, antihyperlipoproteinemic agents, antihypertensives, antihypotensives, anti-infective agents, anti-inflammatory agents, antikeratinizing agents, antimalarial agents, antimicrobial agents, antimigraine agents, antimitotic agents, antimycotic agents, antinauseants, antineoplastic agents, anti-cancer supplementary potentiating agents, antineutropenic agents, antiobsessional agents, antiparasitic agents, antiparkinsonian drugs, antipneumocystic agents, antiproliferative agents, antiprostatic hypertrophydrugs, antiprotozoal agents, antipruritics, antipsoriatic agents, antipsychotics, antirheumatic agents, antischistosomal agents, antiseborrheic agents, antispasmodic agents, antithrombotic agents, antitussive agents, anti-ulcerative agents, anti-urolithic agents, antiviral agents, appetite suppressants, benign prostatic hyperplasia therapy agents, blood glucose regulators, bone resorption inhibitors, bronchodilators, carbonic anhydrase inhibitors, cardiac depressants, cardioprotectants, cardiotonic agents, cardiovascular agents, choleretic agents, cholinergic agents, cholinergic agonists, cholinesterase deactivators, coccidiostat agents, cognition adjuvants and cognition enhancers, depressants, diagnostic aids, diuretics, dopaminergic agents, ectoparasiticides, emetic agents, enzyme inhibitors, estrogens, fibrinolytic agents, free oxygen radical scavengers, gastrointestinal motility agents, glucocorticoids, gonad-stimulating principles, hair growth stimulants, hemostatic agents, histamine H2 receptor antagonists, hormones, hypocholesterolemic agents, hypoglycemic agents, hypolipidemic agents, hypotensive agents, HMGCoA reductase inhibitors, immunizing agents, immunomodulators, immunoregulators, immunostimulants, immunosuppressants, impotence therapy adjuncts, inhibitors, keratolytic agents, LHRH agonists, liver disorder treatments, luteolysin agents, memory adjuvants, mental performance enhancers, mood regulators, mucolytics, mucosal protective agents, mydriatic agents, nasal decongestants, neuroleptic agents, neuromuscular blocking agents, neuroprotective agents, NMDA antagonists, non-hormonal sterol derivatives, oxytocic agents, plasminogen activators, platelet activating factor antagonists, platelet aggregation inhibitors, post-stroke and post-head trauma treatments, potentiators, progestins, prostaglandins, prostate growth inhibitors, prothyrotropin agents, psychotropic agents, radioactive agents, regulators, relaxants, repartitioning agents, scabicides, sclerosing agents, sedatives, sedative-hypnotic agents, selective adenosine A1 antagonists, serotonin antagonists, serotonin inhibitors, serotonin receptor antagonists, steroids, stimulants, suppressants, synergists, thyroid hormones, thyroid inhibitors, thyromimetic agents, tranquilizers, unstable angina agents, uricosuric agents, vasoconstrictors, vasodilators, vulnerary agents, wound healing agents, xanthine oxidase inhibitors, and the like.

In one embodiment, the above-described hydrogel composition contains a whitening agent and thereby acts as a delivery system when applied to the teeth. The release of whitening agents "loaded" into the present hydrogel compositions typically involves both absorption of water and desorption of the agent via a swelling-controlled diffusion mechanism. Whitening agent-containing hydrogel compositions may be employed in a manner similar to that of topical pharmaceutical formulations, for example.

Suitable tooth whitening agents include peroxides, metal chlorites, perborates, percarbonates, peroxyacids, and combinations thereof. Suitable peroxide compounds include hydrogen peroxide, calcium peroxide, magnesium peroxide, carbamide peroxide, and mixtures thereof. The preferred peroxides are hydrogen and carbamide peroxide. Other suitable peroxides include organic peroxides, including but not limited to dialkyl peroxides such as t-butyl peroxide and 2,2 bis(t-butylperoxy)propane, diacyl peroxides such as benzoyl peroxide and acetyl peroxide, peresters such as t-butyl perbenzoate and t-butyl per-2-ethylhexanoate, perdicarbonates such as dicetyl peroxy dicarbonate and dicyclohexyl peroxy dicarbonate, ketone peroxides such as cyclohexanone peroxide and methylethylketone peroxide, and hydroperoxides such as cumene hydroperoxide and tert-butyl hydroperoxide.

The whitening agent is preferably a peroxide, such as hydrogen peroxide or carbamide peroxide, and most preferably is hydrogen peroxide.

Suitable metal chlorites include calcium chlorite, barium chlorite, magnesium chlorite, lithium chlorite, sodium chlorite, and potassium chlorite; hypochlorite and chlorine dioxide. The preferred chlorite is sodium chlorite.

In another embodiment, the pharmaceutically active agent can be, for example, an non-steroidal anti-inflammatory/analgesic; steroidal anti-inflammatory agents; local anesthetics; bactericides/disinfectants; antibiotics; antifungals; tooth desensitizing agents; fluoride anticavity/antidecay agents; anti-tartar/anti-calculus agents; enzymes which inhibit the formation of plaque, calculus or dental caries; abrasive agents such as pyrophosphates; metal chelators such as ethylenediaminetetraacetic acid, tetrasodium salt; anti-oxidants such as butylated hydroxyanisole; butylated hydroxy toluene; nutritional supplements for local delivery to the teeth and surrounding tissue; and so forth.

Suitable non-steroidal anti-inflammatory/analgesic agents include acetaminophen; methyl salicylate; monoglycol salicylate; aspirin; mefenamic acid; flufenamic acid; indomethacin; diclofenac; alclofenac; diclofenac sodium; ibuprofen; flurbiprofen; fentizac; bufexamac; piroxicam; phenylbutazone; oxyphenbutazone; clofezone; pentazocine; mepirizole; and tiaramide hydrochloride.

Suitable steroidal anti-inflammatory agents include hydrocortisone; prednisolone; dexamethasone; triamcinolone acetonide; fluocinolone acetonide; hydrocortisone acetate; prednisolone acetate; methylprednisolone; dexamethasone acetate; betamethasone; betamethasone valerate; flumetasone; fluorometholone; budesonide; and beclomethasone dipropionate.

Suitable local anesthetics include dibucaine hydrochloride; dibucaine; lidocaine hydrochloride; lidocaine; benzocaine; p-buthylaminobenzoic acid 2-(diethylamino) ethyl ester hydrochloride; procaine hydrochloride; tetracaine hydrochloride; chloroprocaine hydrochloride; oxyprocaine hydrochloride; mepivacaine; cocaine hydrochloride; and piperocaine hydrochloride.

Suitable bactericides/disinfectants include thimerosol; phenol; thymol; benzalkonium chloride; benzethonium chloride; chlorhexidine; providone iodide; cetylpyridinium chloride; eugenol, and trimethylammonium bromide.

Suitable antibiotics include penicillin; meticillin; oxacillin; cefalotin; cefaloridin; erythromycin; lincomycin; tetracycline; chlortetracycline; oxytetracycline; metacycline; chloramphenicol; kanamycin; streptomycin; gentamicin; bacitracin; and cycloserine. Suitable antifungal drugs include amphotericin; clotrimazole; econazole nitrate; fluconazole; griseofulvin; itraconazole; ketoconazole; miconazole; nystatin; terbinafine hydrochloride; undecenoic acid; and zinc undecenoate.

Suitable tooth-desensitizing agents include potassium nitrate and strontium chloride. Suitable fluoride anticavity/antidecay agents include sodium fluoride, potassium fluoride and ammonium fluoride.

Additional whitening agents include anti-tartar/anti-calculus agents, including phosphates such as pyrophosphates, polyphosphates, polyphosphonates (e.g., ethane-1-hydroxy-1,1-diphosphonate, 1-azacycloheptane-1,1-diphosphonate, and linear alkyl diphosphonates), and salts thereof; linear carboxylic acids; and sodium zinc citrate; and mixtures thereof. Preferred pyrophosphate salts are the dialkali metal pyrophosphate salts, tetra-alkali metal pyrophosphate salts; and the hydrated or unhydrated forms of disodium dihydrogen pyrophosphate ($Na_2H_2P_2O_7$), tetrasodium pyrophosphate ($Na_4P_2O_7$), and tetrapotassium pyrophosphate ($K_4P_2O_7$). The pyrophosphate salts are described in more detail in Kirk & Othmer, Encyclopedia of Clinical Technology Third Edition, Volume 17, Wiley-Interscience Publishers (1982), the entire disclosure of which is herein incorporated by reference in its entirety. Optionally, whitening agents can also include tartar dissolving agents such as betaines, amine oxides and quaternaries, as described in U.S. Pat. No. 6,315,991 to Zofchak.

Enzymatic agents that would act to inhibit the formation of plaque, calculus or dental caries would also be useful in the compositions. The enzymatic agents can be stored together with the whitening agent, or they can be positioned in a different layer within a multiple layer system as described herein. Suitable enzymes include: proteases that break down salivary proteins which are absorbed onto the tooth surface and form the pellicle, or first layer of plaque; lipases which destroy bacteria by lysing proteins and lipids which form the structural component of bacterial cell walls and membranes; dextranases, glucanohydrolases, endoglycosidases, and mucinases which break down the bacterial skeletal structure which forms a matrix for bacterial adhesion to the tooth; and amylases which prevent the development of calculus by breaking-up the carbohydrate-protein complex that binds calcium. Preferred enzymes include any of the commercially available proteases; dextranases; glucanohydrolases; endoglycosidases; amylases; mutanases; lipases; mucinases; and compatible mixtures thereof. In some embodiments, an enzymatic whitening agent may be utilized.

Optionally, an enzymatic whitening agent is a peroxidase such that peroxide is generated in situ. When an enzymatic whitening or antiplaque agent is incorporated into the composition, the composition should be such that the enzyme is maintained in its active form, e.g., the pH should be approximately neutral, and peroxide may be omitted or contained in a separate layer.

Suitable nutritional supplements for local delivery to the teeth and surrounding tissue include vitamins (e.g., vitamins C and D, thiamine, riboflavin, calcium pantothenate, niacin, folic acid, nicotinamide, pyridoxine, cyanocobalamin, para-aminobenzoic acid, and bioflavonoids); and minerals (e.g., calcium, phosphorus, fluoride, zinc, manganese, and potassium); and mixtures thereof. Vitamins and minerals useful in the present invention are disclosed in *Drug Facts and Comparisons* (loose leaf drug information service), Wolters Kluer Company, St. Louis, Mo., 1997, pp 3-17; the entire disclosure of which is herein incorporated by reference.

The composition can also include any cosmetically active agent. As used herein, a "cosmetically active agent" includes any substance that can be released from the composition to effect a desired change in the appearance of the teeth or surrounding tissue, or which imparts a socially desirable characteristic to the user, such as fresh breath. For example, a cosmetically active agent can be a breath freshener or an agent which effects whitening or bleaching of the teeth. Recognizing that in some cultures or in certain segments of Western society coloration of the teeth may be significant or desirable, the cosmetically active agent can also be any agent which imparts a color or tint to the teeth.

Additional whitening agents may be included in the composition. For example, surfactants such as detergents, may also be present, and will work together with the whitening agents described above to provide a brighter appearance to the teeth.

In any of these embodiments, a tooth whitening composition of the invention preferably includes a peroxide for whitening the teeth, and may also include conventional additives such as fillers, preservatives, pH regulators, softeners, thickeners, colorants, pigments, dyes, refractive particles, stabilizers, toughening agents, pharmaceutical agents, flavoring or breath freshening agents, and permeation enhancers. In those embodiments wherein adhesion is to be reduced or eliminated, conventional detackifying agents may also be used. These additives, and amounts thereof, are selected in such a way that they do not significantly interfere with the desired chemical and physical properties of the tooth whitening composition, or interfere with the delivery of the tooth whitening agent can be included in the composition. Such additional ingredients include coloring compounds; food additives, flavorants, sweeteners, and preservatives.

E. Other Ingredients

Any natural or synthetic flavorant or food additive, such as those described in Chemicals Used in Food Processing, Pub. No. 1274, National Academy of Sciences, pages 63-258 (the entire disclosure of which is herein incorporated by reference) can be included in the compositions of the invention. Suitable flavorants include wintergreen, peppermint, spearmint, menthol, fruit flavors, vanilla, cinnamon, spices, flavor oils and oleoresins, as known in the art, as well as combinations thereof. The amount of flavorant employed is normally a matter of preference, subject to such factors as flavor type, individual flavor, and strength desired. Preferably, the composition comprises from about 0.1 to 5 wt % flavorant.

Sweeteners useful in the present invention include sucrose, fructose, aspartame, xylitol and saccharine. Preferably, the composition comprises sweeteners in an amount from about 0.001 to 5.0 wt %.

The suitable substrate can be translucent so that the composition is unobtrusive when worn. However, the substrate or the composition can optionally be colored, so that the composition is easily seen when worn. Preferably, if coloring is desired, the color will be present in the substrate. For example, the substrate can be colored with bright or vibrant colors which a consumer may find pleasing. The substrate can therefore comprise a colorizing compound, such as, for example, a dye, pigment or substance that can impart color when added to the material forming the substrate.

For example, colorizing compounds of the type commonly used with a food, drugs, or cosmetics in connection with the human body, especially color additives permitted for use in foods which are classified as "certifiable" or "exempt from certification," can be used to color the substrate. The colorizing compounds used to color the substrate can be derived from natural sources such as vegetables, minerals or animals, or can be man-made counterparts of natural derivatives.

Colorizing compounds presently certified under the Food Drug & Cosmetic Act for use in food and ingested drugs include dyes such as FD&C Red No. 3 (sodium salt of tetraiodofluorescein); Food Red 17 (disodium salt of 6-hydroxy-5-{(2-methoxy-5-methyl-4-sulphophenyl)azo}-2-naphthalenesulfonic acid); Food Yellow 13 (sodium salt of a mixture of the mono and disulfonic acids of quinophthalone or 2-(2-quinolyl)indanedione); FD&C Yellow No. 5 (sodium salt of 4-p-sulfophenylazo-1-p-sulfophenyl-5-hydroxypyrazole-3 carboxylic acid); FD&C Yellow No. 6 (sodium salt of p-sulfophenylazo-B-napthol-6-monosulfonate); FD&C Green No. 3 (disodium salt of 4-{[4-(N-ethyl-p-sulfobenzylamino)-phenyl]-(4-hydroxy-2-sulfonium-phenyl)-methylene}-[1-(N-ethyl-N-p-sulfobenzyl)-3,5-cyclohexadienimine]); FD&C Blue No. 1 (disodium salt of dibenzyldiethyldiaminotriphenylcarbinol trisulfonic acid anhydrite); FD&C Blue No. 2 (sodium salt of disulfonic acid of indigotin); FD&C Red No. 40; Orange B; and Citrus Red No. 2; and combinations thereof in various proportions.

Colorizing compounds exempt from FDA certification include annatto extract; betaapo-8'-carotenal; beta-carotene; beet powder; canthaxanthin; caramel color; carrot oil; cochineal extract (carmine); toasted, partially defatted, cooked cottonseed flour; ferrous gluconate; fruit juice; grape color extract; grape skin extract (enocianina); paprika; paprika oleoresin; riboflavin; saffron; turmeric; turmeric oleoresin; vegetable juice; and combinations thereof in various proportions.

The form of the colorizing compound for use in the composition preferably includes dye form additives, but may also include lake forms which are compatible with the material comprising the substrate. Water soluble dyes, provided in the form of powders, granules, liquids or other special-purpose forms, can be used in accordance with the present method. Preferably, the "lake", or water-insoluble form of the dye, is used for coloring the substrate. For example, if a suspension of a colorizing compound is to be used, a lake form additive can be employed. Suitable water-insoluble dye lakes prepared by extending calcium or aluminum salts of FD&C dyes on alumina include FD&C Green #1 lake, FD&C Blue #2 lake, FD&C R&D #30 lake and FD&C # Yellow 15 lake.

Other suitable colorizing compounds include non-toxic, water-insoluble inorganic pigments such as titanium dioxide; chromium oxide greens; ultramarine blues and pinks; and ferric oxides. Such pigments preferably have a particle size in the range of about 5 to about 1000 microns, more preferably about 250 to about 500 microns.

The concentration of the colorizing compound in the substrate is preferably from about 0.05 to 10 wt %, and is more preferably from about 0.1 to 5 wt %.

More than one colorizing compound can be present in the substrate, so that multiple colors are imparted therein. These multiple colors can be patterned into stripes, dots, swirls, or any other design which a consumer may find pleasing. The colorizing compound can also be used with other appearance-enhancing substances such as glitter particles.

Absorbent fillers may be advantageously incorporated to control the degree of hydration when the adhesive is on the tooth surface. Such fillers can include microcrystalline cellulose, talc, lactose, kaolin, mannitol, colloidal silica, alumina, zinc oxide, titanium oxide, magnesium silicate, magnesium aluminum silicate, hydrophobic starch, calcium sulfate, calcium stearate, calcium phosphate, calcium phosphate dihydrate, clays such as laponite, woven and non-woven paper and cotton materials. Other suitable fillers are inert, i.e., substantially nonadsorbent, and include, for example, polyethylenes, polypropylenes, polyurethane polyether amide copolymers, polyesters and polyester copolymers, nylon and rayon. A preferred filler is colloidal silica, e.g., Cab-O-Sil® (Cabot Corporation, Boston Mass.).

Preservatives include, by way of example, p-chloro-m-cresol, phenylethyl alcohol, phenoxyethyl alcohol, chlorobutanol, 4-hydroxybenzoic acid methylester, 4-hydroxybenzoic acid propylester, benzalkonium chloride, cetylpyridinium chloride, chlorohexidine diacetate or gluconate, ethanol, and propylene glycol.

Compounds useful as pH regulators include, but are not limited to, glycerol buffers, citrate buffers, borate buffers, phosphate buffers, or citric acid-phosphate buffers may also be included so as to ensure that the pH of the hydrogel composition is compatible with that of the environment of the mouth and will not leach minerals from the surface of the teeth. In order to optimize whitening without demineralization of the teeth, calcium and/or fluoride salts can be included in the composition.

Suitable softeners include citric acid esters, such as triethylcitrate or acetyl triethylcitrate, tartaric acid esters such as dibutyltartrate, glycerol esters such as glycerol diacetate and glycerol triacetate; phthalic acid esters, such as dibutyl phthalate and diethyl phthalate; and/or hydrophilic surfactants, preferably hydrophilic non-ionic surfactants, such as, for example, partial fatty acid esters of sugars, polyethylene glycol fatty acid esters, polyethylene glycol fatty alcohol ethers, and polyethylene glycol sorbitan-fatty acid esters.

Preferred thickeners herein are naturally occurring compounds or derivatives thereof, and include, by way of example: collagen; galactomannans; starches; starch derivatives and hydrolysates; cellulose derivatives such as methyl cellulose, hydroxypropylcellulose, hydroxyethyl cellulose, and hydroxypropyl methyl cellulose; colloidal silicic acids; and sugars such as lactose, saccharose, fructose and glucose. Synthetic thickeners such as polyvinyl alcohol, vinylpyrrolidone-vinylacetate-copolymers, polyethylene glycols, and polypropylene glycols may also be used.

The substrate can also be embedded or decorated with decorative items such as beads, rhinestones, or the like, as long as these items do not interfere with the visco-elastic properties of the substrate required for proper deformation of the composition onto the teeth, as described above. The substrate can also display letters, words, or images designed to be pleasing or attractive to a consumer.

F. Erodible Backing Member

The erodible backing member is comprised of a polymer composition that erodes in a moist environment at a slower rate than the hydrogel and is substantially non-tacky. There are numerous materials that can be used for the backing member, and include, by way of example, and not limitation, acrylate polymers, cellulose derived polymers, cellulose esters, starches, alginic acid, alginates, polyamino acids. Combinations, i.e., Blends of any of these different polymers can also serve as backing member material.

In one embodiment, the hydrogel erodes in about 1 second to 24 hours after placement in a moist environment, and in another embodiment the hydrogel erodes about 10 seconds to 8 hours after placement. The erodible backing member, in one embodiment, erodes about 12 to 24 hours after the hydrogel has eroded, while in another embodiment the backing erodes within about 12 hours after hydrogel has eroded. The erodible backing member material can be selected so as to erode at a slightly slower or approximately the same rate (e.g., when they both erode within about 24 hours), but is preferably selected so that it erodes at a slower rate than the hydrogel composition, when in use. In one embodiment, the erodible backing member erodes at least about 200% slower than the hydrogel, in another embodiment, the backing erodes at least about 100% slower, in a different embodiment the backing erodes at least about 50% slower, and in yet another embodiment the backing erodes at least about 25% slower than the hydrogel.

Suitable acrylate polymers are described above as waterswellable, water-insoluble polymers, and include by way of example and not limitation, polymers formed from acrylic acid, methacrylic acid, methyl acrylate, ethyl acrylate, methyl methacrylate, ethyl methacrylate, and/or other vinyl monomers. Preferred acrylate polymers are the Eudragit® copolymers (copolymers of methacrylic acid and methyl methacrylate), such as the Eudragit® series E, L, S, RL, RS and NE copolymers. As noted above, these Eudragit polymers also find utility as the waterswellable, water-insoluble polymer component of the hydrogel. Since Eudragit polymers are available in different grades with varying pH dependent solubility and permeability characteristics, the grade used for the erodible backing can be selected to have a lower solubility as compared to the grade used in the hydrogel. For example, if L 100-55 is selected for use in the hydrogel, Eudragit L 100 can be used in the backing; if Eudragit L 100 is used in hydrogel, Eudragit S 100 could be used in the backing; and so forth. In addition, mixtures of Eudragit polymers or mixtures of Eudragit polymers with other polymers and excipients (e.g. buffering agents, pH modulators) may be used to tailor the rate of erosion of the backing member relative to the hydrogel.

Suitable cellulose derived polymers include by way of example and not limitation, hydratecellulose (cellophane), methyl cellulose, ethyl cellulose, hydroxyethyl cellulose (HEC), hydroxypropylcellulose (HPC), hydroxypropylmethylcellulose (HPMC), carboxymethylcellulose (CMC), and sodium carboxymethylcellulose (Na-CMC). Preferred celluloses are hydratecellulose, methyl cellulose, ethyl cellulose, hydroxyethyl cellulose, hydroxypropylcellulose, hydroxypropylmethylcellulose, carboxymethylcellulose, sodium carboxymethylcellulose, and mixtures thereof.

Suitable cellulose esters are described above as waterswellable, water-insoluble polymers, and include by way of example and not limitation, cellulose acetate, cellulose acetate propionate, cellulose acetate butyrate, cellulose propionate, cellulose butyrate, cellulose propionate butyrate, cellulose diacetate, cellulose triacetate, and mixtures, polymers and copolymers thereof. Exemplary cellulose ester copolymers include cellulose acetate butyrate and cellulose acetate proprionate. Preferred cellulose esters are cellulose acetate, cellulose acetate propionate, cellulose acetate butyrate, cellulose propionate, cellulose butyrate, cellulose propionate butyrate, cellulose diacetate, cellulose triacetate, cellulose acetate butyrate, and cellulose acetate proprionate and mixtures thereof.

Suitable starches include by way of example and not limitation, potato starch acetate, maize starch, etc (e.g., Clearam® starches sold by Roquette), and mixtures thereof.

Suitable alginates include by way of example and not limitation, propylene glycol alginate, sodium alginate, calcium alginate, and so forth, as well as mixtures thereof.

Suitable polyamino acids include by way of example and not limitation, polylysine, polyglycine, polyalanine, protamine, and so forth, as well as mixtures thereof.

It is understood that any of the active agents and other ingredients described in relation to the hydrogel composition can also be present in the backing member. For example, the hydrogel may contain an active agent that is released onto a tooth surface or oral mucosa, while the backing can be loaded with a flavorant, which is released to oral cavity.

IV. Fabrication Processes

The hydrogel compositions of the invention are generally melt extrudable, and thus may be prepared using a simple blending and extruding process. The components of the composition are weighed out and then admixed, for example using a Brabender or Baker Perkins Blender, generally although not necessarily at an elevated temperature, e.g., about 90 to 140° C. Solvents or water may be added if desired. The resulting composition can be extruded using a single or twin extruder, or pelletized. Alternatively, the components of the hydrogel composition can be melted one at a time, and then mixed prior to extrusion. The hydrogel composition can be extruded directly onto the erodible backing member. The hydrogel composition can be also extruded first, and then be pressed against the backing member or laminated to the backing member. A releasable liner may also be included. The thickness of the resulting hydrogel-containing film, for most purposes, will be in the range of about 0.050 to 0.80 mm, more usually in the range of about 0.37 to 0.47 mm.

Alternatively, the compositions may be prepared by solution casting, by admixing the components of the composition in a suitable solvent, e.g., a volatile solvent such as ethyl acetate, or lower alkanols (e.g., ethanol, isopropyl alcohol, etc.) are particularly preferred, at a concentration typically in the range of about 35 to 60% w/v. The solution is cast onto the erodible backing member or releasable liner, as above. Both admixture and casting are preferably carried out at ambient temperature. The backing member coated with the film is then baked at a temperature in the range of about 80 to 100° C., optimally about 90° C., for time period in the range of about one to four hours, optimally about two hours. Accordingly, one embodiment of the invention is a method for preparing a hydrogel film suitable for incorporation into a composition of the invention, which involves the following steps: preparing a solution of a water-swellable, water-insoluble polymer, a hydrophilic polymer, and a complementary oligomers capable of hydrogen or electrostatic bonding to the hydrophilic polymer, in a solvent; depositing a layer of the solution on an erodible backing member to provide a coating thereon; and heating the coated backing member to a temperature in the range of about 80 to 100° C. for a time period in the range of about 1 to 4 hours, thereby providing a hydrogel film on the backing member.

When tacky hydrogel compositions are desired, solution casting is the preferred process. For preparation of substantially nontacky compositions, melt extrusion is preferred. Either melt extrusion or solution casting techniques can be used to prepare translucent compositions, although solution casting is typically preferred for these embodiments. Accordingly, another embodiment of the invention is a method of forming a composition comprised of a continuous hydrophilic phase, which involves the following steps: melt processing through an extruder a mixture of a water-swellable, water-insoluble polymer, a hydrophilic polymer, and a complementary oligomer capable of hydrogen or electrostatic bonding to the hydrophilic polymer, to form an extruded composition; extruding the composition as a film of desired thickness onto a suitable erodible backing member; and, when cooled, and loading the film with an aqueous solution of the active agent such as a peroxide to obtain a concentration of whitening agent of from about 1 to 20 wt %.

The invention also contemplates having a multiple layer system that includes one or more additional hydrogel or non-hydrogel layers. For example, it may be desirable to include additional active agents that may not be compatible with the primary active agent during storage. In this manner, one layer can be the primary active agent-containing hydrogel layer and the other layer(s) can contain additional actives. These other layers can be made of the hydrogel composition described herein, or any other biocompatible formulation known in the art (e.g., polyisobutylene, dimethyl siloxane, ethylene vinyl acetate, polyvinylacetate, cellulose acetate, butyrate, propionate, ethyl cellulose and water-insoluble acrylates). In addition, depending on ordering of the layers, it may be desired to have a tacky layer, e.g., the layer to be positioned directly on the teeth, and a non-tacky layer, e.g., the outer layer that is positioned nearest the lips. Another advantage of having multiple layer system is that the ratio of polymers used in the outermost layer can be varied to achieve a non-tacky layers so as to avoid having to include a separate backing layer in the product.

In one embodiment, the composition comprises: an outer erodible backing member that serves as the external surface of the composition following application to the tooth, oral tissue or mucosal surface; a surface contact adhesive layer adhered thereto, which generally will be an adhesive composition of the invention, optionally containing additional active agents; and a removable release liner. Upon removal of a release liner, for example, the composition is applied to the surface, e.g., the teeth, to be treated, and placed on the surface so that the oral surface-contacting layer is in contact with the teeth or other oral surface. In another embodiment, the composition is packaged without a release liner. Accordingly, once removed from the packaging, the composition is ready to be applied to the oral surface.

The hydrogel-erodible backing member composition may comprise an additional substrate layer, which can serve as the primary structural element and provide the composition with support, either during manufacture or during use. The material used for the substrate should be inert and incapable of absorbing the hydrogel-erodible backing member composition. Also, the material used for the substrate should permit the device to follow the contours of the teeth or other body surface and be worn comfortably in the mouth without rubbing or otherwise irritating the lips or tongue. Examples of materials useful for the substrate are polyesters, polyethylene, polypropylene, polyurethanes and polyether amides. The substrate is preferably in the range of about 15 microns to about 250 microns in thickness, and may, if desired, be pigmented, metallized, or provided with a matte finish suitable for writing.

In one embodiment, the substrate is preferably although not necessarily occlusive (i.e., not "breathable"), and does not allow any active agent in the composition to leak through the layer, and contact the mucous membranes of the mouth and gums. When ready for use, the composition is pre-moistened so that the tackiness is increased and the composition will adhere to the teeth. One advantage of this embodiment is that the active agent cannot substantially leak out through the substrate and cause irritation in those individuals sensitive to the active agent or to any unpleasant flavor or sensation.

Other suitable substrate materials can be non-polymeric materials such as waxes (e.g., microcrystalline or paraffin waxes) a or wax/foam laminate. Paraffin waxes are low molecular weight straight-chain hydrocarbons, with melting points of about 48-75° C. and molecular weights of about 300-1400 g/mol, and are typically made by the Fischer-Tropsch synthesis. Microcrystalline waxes are flexible and amorphous-like in appearance and tend to have a higher tensile strength and smaller crystal size than paraffin waxes. Microcrystalline waxes typically have melting points of about 60-95° C. and molecular weights of about 580-700 g/mol, and predominantly contain branched-chain hydrocarbons and some ring-type compounds, although straight-chain hydrocarbons can be present. The substrate material can also be an open-cell foam such as a polyurethane, polystyrene or polyethylene foam.

Alternatively, in another embodiment, the substrate is non-occlusive, and therefore can fully hydrate in situ, in position on the teeth or other body surface.

The release liner is a disposable element that serves to protect the system prior to application. The release liner should be formed from a material impermeable to the active agent and hydrogel composition, and that is easily stripped from the contact adhesive. Release liners are typically treated with silicone or fluorocarbons, and are commonly made from polyesters and polyethylene terephthalate.

A preferred composition is typically prepared using an acrylate polymer as the water-insoluble, water-swellable polymer; and a blend of polyvinylpyrrolidone and polyethylene glycol as the blend of a hydrophilic polymer with a complementary oligomer capable of hydrogen or electrostatic bonding to the hydrophilic polymer.

An adhesive film of the composition can be manufactured by thermally melting and mixing the above components together at temperatures ranging from about 100 to 170° C. The film is extruded to a desired thickness on a suitable substrate. Alternatively, the components can be dissolved in a single or mixture of solvents, and the solution can be cast on a releasing or backing film. The solvents are then evaporated to obtain a hydrogel film.

One method of loading the composition with the active agent comprises layering a desired active agent, e.g., a tooth whitening agent, in aqueous solution onto the surface of the hydrogel placed on a suitable substrate, or to place the active agent directly on the substrate. The release liner is then assembled on top of the composition, forming a sandwich structure, and the solution containing the whitening agent is absorbed into the composition due to its water-swellable properties. Alternatively, the composition layered onto the substrate can be submerged in a solution containing the desired concentration of whitening agent, and the solution absorbed into the composition. By measuring the rate of weight gain on absorbing the liquid, the percent loading of the composition with the active agent can be determined and controlled.

Another approach to loading the active agent into the composition is to add the active agent as a solid or as a solution to the composition dissolved in solvent. The mixture is then cast as usual onto a suitable substrate and allowed to dry, although a lower drying temperature is desired when using this method of loading. Compositions prepared in this manner can be dried at ambient temperature for a time period ranging from about 1 hour to several days.

A typical film thickness is from about 0.050 to 0.80 mm, preferably 0.25 to 0.50 mm. The thickness of the film is not critical, and can be varied according to the concentration of whitening agent incorporated into the film, the length of time the film is to be exposed to the teeth, the level of comfort desired by the wearer, and the degree of staining that it is desired to rectify.

V. Methods of Use

In practice, the compositions can be used simply by removing the product from its package, removing a release liner (when included) and applying the adhesive layer to the teeth that it is desired to whiten (or placed in any moist body environment or moist surface if another utility of the composition is to be used or if another active agent is to be used). The systems described herein can be provided in a variety of sizes, so that the composition can be applied to the entirety or any portion of a tooth, to any number of teeth at one time, or to any portion of the oral cavity or other moist area.

The backing member can be formulated to be occlusive or impermeable to the active agent so as to reduce or prevent leakage of the active agent, from the composition, while the user wears the composition for the desired amount of time, i.e., the composition will then deliver the drug uni-directionally, e.g., only towards the mucosal tissue. Alternately, the backing member can be formulated to have a predetermined permeability so as to provide for bi-directional drug delivery, e.g., towards the mucosal surface as well as towards the oral cavity. The level of permeability, i.e., its selective nature, can also be used to control the relative rates of delivery towards the mucosal surface and the oral cavity.

The composition can be maintained in the desired location for as little time as a few minutes, several hours, all day or overnight, and then removed when the desired degree of whitening or the desired therapeutic or cosmetic effect has been achieved. Alternately, the composition can be left in place and allowed to erode entirely. Accordingly, in one embodiment of the invention, a method for whitening teeth may simply comprise applying the composition to teeth in need of whitening, while in another embodiment, the method may further comprise removing the composition when the desired degree of whitening has been achieved.

If desired, a translucent composition can be provided, and is worn without being obtrusive or noticeable to others. The system can also be designed without an active ingredient and finds utility as a protective dressing for an oral surface, e.g., as a wound dressing.

The composition can be worn for an extended period of time, but will typically be worn for a predetermined period of time of from about 10 minutes to about 24 hours, after which the composition can be removed or will have eroded away. For tooth whitening applications, a preferred time period is from about 10 minutes to about 8 hours (e.g., overnight), with 30 minutes to about 1 hour also being a preferred embodiment. For other active agents, a therapeutically or cosmeceutically effective time can be readily determined based upon the active agent that is being used as well as the condition being treated.

In one embodiment, the hydrogel is a solid and is attached to the backing member during manufacture. Accordingly, the composition is applied in a single step. Alternately, the hydrogel can be a non-solid and manufactured and packaged separate from the backing member. In that instance, the hydrogel is first applied by the user, followed by the user applying the backing member to the outer surface of the hydrogel. In either embodiment, the user can form the composition around the upper or lower teeth or other oral tissue by applying normal manual pressure to the backing member with the tips of the fingers and thumbs, optionally by slightly moistening the composition or the body surface prior to application. Assuming the surface area of the average adult finger or thumb tip is approximately one square centimeter, the normal pressure generated by the finger and thumb tips is about 100,000 to about 150,000 Pascals (i.e., about 3 lbs. or 1.36 kg) per square centimeter. The pressure is typically applied to the composition by each finger and thumb tip for about one or two seconds. Once the pressure applied to the backing member by the tips of the fingers and thumbs is removed, the composition remains in the shape of, and adherent to, the surface of the teeth and adjoining soft tissue onto which it was formed.

When the user is ready to remove the composition, the composition can be removed simply by peeling it away from the surface of the teeth or other oral or body surface. If desired, the composition can be re-adhered for additional treatment time. Any residue left behind is minimal, and can be removed using conventional tooth or oral cavity cleansing methods.

In one embodiment of the invention, the composition is a solid and is a pressure sensitive adhesive and absorbs water.

The composition can also be applied as a non-solid composition, for example applied as a liquid or gel. For example, the user can extrude the composition from a tube onto a finger for application to the teeth or other body surface, extrude the composition from a tube directly onto the teeth, apply the composition by means of a brush or other applicator, and so forth. The erodible backing member can then be applied as separate step after the liquid or gel is applied. After the evaporation of solvent, the liquid or gel composition dries to form a matrix-type polymer film or gel on the body surface. In one embodiment of this liquid or gel film-former composition, the hydrogel contains sufficient water or other solvent to provide flowable property. In another embodiment of this composition, the polymer components of the liquid or gel composition are soluble in a water-ethanol mixture both at ambient temperature and at refrigeration temperatures of about 4° C., and are miscible upon solvent evaporation. In yet another embodiment of this liquid or gel film-former composition, the polymeric composition has a Lower Critical Solution Temperature of about 36° C. in an ethanol-water mixture. The resulting film (after solvent evaporation) is preferably insoluble or slowly soluble in saliva at body temperature so as to provide long lasting contact between the hydrogen peroxide and the dental enamel. Finally, the hydrogen peroxide should be stable both in the liquid or gel composition, as well as within polymer film upon drying.

The practice of the present invention will employ, unless otherwise indicated, conventional techniques of polymer chemistry, adhesive manufacture, and hydrogel preparation, which are within the skill of the art. Such techniques are fully explained in the literature.

It is to be understood that while the invention has been described in conjunction with the preferred specific embodiments thereof, the foregoing description, as well as the examples that follow, are intended to illustrate and not limit the scope of the invention. Other aspects, advantages and modifications will be apparent to those skilled in the art to which the invention pertains. All patents, patent applications, journal articles and other references cited herein are incorporated by reference in their entireties.

The following examples are put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperatures, etc.) but some errors and deviations should be accounted for. Unless indicated otherwise, parts are parts by weight, temperature is in degrees Celsius (° C.), and pressure is at or near atmospheric.

The following abbreviations and tradenames are used in the examples:

| | |
|---|---|
| Eudragit L 100-55 | methacrylic acid copolymer (Rohm America Inc.) |
| Eudragit L 100 | methacrylic acid copolymer (Rohm America Inc.) |
| PEG | polyethylene glycol 400 |
| PVP | Kollidon ® 90 polyvinylpyrrolidone (BASF) |

EXAMPLES

Example 1

Preparation of a Solid Composition

One embodiment of a composition for tooth whitening can be prepared from the following ingredients using a melt extrusion process:

| | |
|---|---|
| Eudragit L 100-55 | 9 wt % |
| PVP | 44 wt % |
| PEG | 22 wt % |
| Hydrogen peroxide | 6 wt % |
| Water, stabilizers, pH modulators | 19 wt % |

The ingredients are melt processed in a Brabender single screw extruder as follows:

The Eudragit L 100-55 is added to the extruder first, followed by PVP and PEG, at a temperature of 100 to 150° C. The composition is extruded to a thickness of 0.35 mm between a polyethylene terephthalate release liner and an erodible backing member made of Eudragit S 100 with appropriate plasticizer if needed. Hydrogen peroxide solution was added to the extruded film.

Example 2

Preparation of a Non-Solid Composition

A composition for tooth whitening is prepared from the following ingredients:

| | |
|---|---|
| Deionized water | 35.0 wt % |
| Ethanol | 35.0 wt % |
| Eudragit L 100-55 | 4.00 wt % |
| PEG | 1.00 wt % |
| PVP | 7.00 wt % |
| Carbamide peroxide | 18.0 wt % |
| Sodium citrate | 0.13 wt % |

The composition is mixed in a Cole-Parmer high-torque low-speed lab mixer supplied with Teflon coated impeller (2 inches in diameter) as follows. Deionized water is mixed with ethanol, followed by the addition of PEG. Sodium citrate is then added under vigorous stirring conditions. Eudragit L 100-55 powder is added slowly (within 2-5 min) under vigorous stirring (500-600 rpm). After about 5-10 min (it is not necessary to wait until all Eudragit is dissolved), PVP powder is slowly added (within 5 min). The high stirring rate is maintained over 5-10 min. Carbamide peroxide powder was added (within 1-2 min) and the mixture stirred to obtain a homogeneous solution (approximately 30 minutes at 800-900 rpm). The solution is then stored over a period of 2-5 hours to let the air bubbles dissipate.

This tooth whitening composition can be packaged for use with a Eudragit RL 100 erodible backing member.

Example 3

Preparation of a Non-Solid Composition

A composition for tooth whitening is prepared from the following ingredients:

| | |
|---|---|
| Deionized water | 35.0 wt % |
| Ethanol | 35.0 wt % |
| Eudragit L 100-55 | 2.50 wt % |
| PEG | 1.92 wt % |
| PVP | 6.00 wt % |
| Carbamide peroxide | 18.0 wt % |
| Sodium Citrate | 0.08 wt % |
| Methocel A4C | 1.50 wt % |

The composition is mixed in a Cole-Parmer high-torque low-speed lab mixer supplied with Teflon coated impeller (2 inches in diameter). Deionized water is mixed with ethanol, followed by the addition of PEG. Sodium citrate is then added under vigorous stirring conditions. Eudragit L 100-55 powder is added slowly (within 5 min) under vigorous stirring (500-600 rpm), followed by the slow (within 5 min) addition of Methocel A4C powder under vigorous stirring (500-600 rpm). After about 10 min, PVP powder is slowly added (within 5 min). The high stirring rate is maintained over 5-10 min. Carbamide peroxide powder is added (within 1-2 min) and the mixture stirred to obtain a homogeneous solution (approximately 30-60 minutes at 500-800 rpm). The solution is then stored over a period of 2-5 hours to let the air bubbles dissipate.

This tooth whitening composition can be packaged for use with a Eudragit RS 100 erodible backing member.

We claim:

1. A composition, comprising:
   (a) a hydrogel comprising:
      (i) a water-swellable, water-insoluble acrylate polymer which is a copolymer of methacrylic acid and methyl methacrylate and is insoluble in aqueous fluid having a pH of 5.5 or below;
      (ii) a blend of a hydrophilic polymer with a complementary oligomer capable of hydrogen or electrostatic bonding to the hydrophilic polymer; and
      (iii) an active agent; and
   (b) a backing member comprising a material selected from acrylate polymers, starches, alginic acid, alginates, polyamino acids, and combinations thereof, wherein said backing member erodes in a moist environment at a slower rate than the hydrogel.

2. A composition, comprising:
   (a) a hydrogel comprising:
      (i) a water-swellable, water-insoluble cellulose ester polymer which renders the hydrogel tacky prior to application to a moist surface, but nontacky upon absorption of water;
      (ii) a blend of a hydrophilic polymer with a complementary oligomer capable of hydrogen or electrostatic bonding to the hydrophilic polymer; and
      (iii) an active agent; and
   (b) a backing member that erodes in a moist environment at a slower rate than the hydrogel.

3. A composition, comprising:
   (a) a hydrogel comprising:
      (i) a water-swellable alginic acid polymer which is insoluble in aqueous fluid having a pH of 5.5 or below;
      (ii) a blend of a hydrophilic polymer with a complementary oligomer capable of hydrogen or electrostatic bonding to the hydrophilic polymer; and
      (iii) an active agent; and
   (b) a backing member that erodes in a moist environment at a slower rate than the hydrogel.

4. A method for whitening teeth while minimizing tooth sensitivity, wherein said method comprises applying to teeth a composition comprising:
   (a) a hydrogel comprising:
      (i) a water-swellable, water-insoluble acrylate polymer which is a copolymer of methacrylic acid and methyl methacrylate and is insoluble in aqueous fluid having a pH of 5.5 or below;
      (ii) a blend of a hydrophilic polymer with a complementary oligomer capable of hydrogen or electrostatic bonding to the hydrophilic polymer; and
      (iii) an active agent; and
   (b) a backing member comprising a material selected from acrylate polymers, starches, alginic acid, alginates, polyamino acids, and combinations thereof, wherein said backing member erodes in a moist environment at a slower rate than the hydrogel.

5. A method for whitening teeth while minimizing tooth sensitivity, wherein said method comprises applying to teeth a composition comprising:
   (a) a hydrogel comprising:
      (i) a water-swellable, water-insoluble cellulose ester polymer which renders the hydrogel tacky prior to application to a moist surface, but nontacky upon absorption of water;
      (ii) a blend of a hydrophilic polymer with a complementary oligomer capable of hydrogen or electrostatic bonding to the hydrophilic polymer; and
      (iii) an active agent; and
   (b) a backing member that erodes in a moist environment at a slower rate than the hydrogel.

6. A method for whitening teeth while minimizing tooth sensitivity, wherein said method comprises applying to teeth a composition comprising:
   (a) a hydrogel comprising:
      (i) a water-swellable alginic acid polymer which is insoluble in aqueous fluid having a pH of 5.5 or below;
      (ii) a blend of a hydrophilic polymer with a complementary oligomer capable of hydrogen or electrostatic bonding to the hydrophilic polymer; and
      (iii) an active agent; and
   (b) a backing member that erodes in a moist environment at a slower rate than the hydrogel.

* * * * *

UNITED STATES PATENT AND TRADEMARK OFFICE
CERTIFICATE OF CORRECTION

PATENT NO. : 8,741,331 B2  
APPLICATION NO. : 13/916526  
DATED : June 3, 2014  
INVENTOR(S) : Singh et al.

Page 1 of 1

It is certified that error appears in the above-identified patent and that said Letters Patent is hereby corrected as shown below:

Title page under item (71) Applicant: add --A.V. Topchiev Institute of Petrochemical Synthesis, Moscow (RU)--

Title page under item (73) Assignees: change "A.V. Topchiev Institute of Petrochemicals Synthesis, Russian Academy of Sciences, Moscow (RU)" to --A.V. Topchiev Institute of Petrochemical Synthesis, Russian Academy of Sciences, Moscow (RU)--

Signed and Sealed this  
Fourteenth Day of October, 2014

Michelle K. Lee  
*Deputy Director of the United States Patent and Trademark Office*